(12) United States Patent
Helson et al.

(10) Patent No.: US 10,258,691 B2
(45) Date of Patent: *Apr. 16, 2019

(54) PROTECTIVE EFFECT OF DMPC, DMPG, DMPC/DMPG, EGPG, LYSOPG AND LYSOPC AGAINST DRUGS THAT CAUSE CHANNELOPATHIES

(71) Applicants: SignPath Pharma Inc., Quakertown, PA (US); Avanti Polar Lipids, Inc., Alabaster, AL (US)

(72) Inventors: Lawrence Helson, Quakertown, PA (US); George M. Shopp, Boulder, CO (US); Annie Bouchard, Stoke (CA); Muhammed Majeed, East Windsor, NJ (US); Stephen W. Burgess, Chelsea, AL (US); Walter A. Shaw, Birmingham, AL (US)

(73) Assignee: Signpath Pharma, Inc., Sandy, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/729,940

(22) Filed: Jun. 3, 2015

(65) Prior Publication Data
US 2015/0343063 A1    Dec. 3, 2015

Related U.S. Application Data

(60) Provisional application No. 62/007,244, filed on Jun. 3, 2014, provisional application No. 62/035,417, filed on Aug. 9, 2014, provisional application No. 62/056,957, filed on Sep. 29, 2014, provisional application No. 62/150,059, filed on Apr. 20, 2015.

(51) Int. Cl.
| *A61K 9/127* | (2006.01) |
| *A61K 45/06* | (2006.01) |
| *G01N 33/68* | (2006.01) |
| *A61K 31/506* | (2006.01) |
| *A61K 31/20* | (2006.01) |
| *A61K 31/23* | (2006.01) |
| *A61K 31/683* | (2006.01) |
| *A61K 31/685* | (2006.01) |
| *G01N 33/50* | (2006.01) |

(52) U.S. Cl.
CPC ............. *A61K 45/06* (2013.01); *A61K 9/127* (2013.01); *A61K 31/20* (2013.01); *A61K 31/23* (2013.01); *A61K 31/506* (2013.01); *A61K 31/683* (2013.01); *A61K 31/685* (2013.01); *G01N 33/5008* (2013.01); *G01N 33/6872* (2013.01); *G01N 33/6887* (2013.01); *G01N 2800/32* (2013.01)

(58) Field of Classification Search
None
See application file for complete search history.

(56) References Cited

U.S. PATENT DOCUMENTS

| 6,143,321 A | 11/2000 | Needham et al. |
| 6,787,132 B1 | 9/2004 | Gabizon et al. |
| 6,946,475 B1 | 9/2005 | Lloyd |
| 8,642,074 B2 | 2/2014 | Mei et al. |
| 8,747,890 B2 | 6/2014 | Helson |
| 8,753,674 B2 * | 6/2014 | Helson .................. A61K 9/127 424/450 |
| 9,138,411 B2 | 9/2015 | Ranjan et al. |
| 2002/0110586 A1 | 8/2002 | Madden et al. |
| 2005/0101674 A1* | 5/2005 | Maurer .................. A61K 31/16 514/625 |
| 2006/0269595 A1 | 11/2006 | Madden |
| 2009/0291134 A1 | 11/2009 | Ateeq et al. |
| 2010/0068251 A1 | 3/2010 | Ali et al. |
| 2010/0120890 A1 | 5/2010 | Fedida |
| 2010/0291043 A1 | 11/2010 | Medin et al. |
| 2014/0050780 A1* | 2/2014 | Cerundolo ......... A61K 39/0011 424/450 |

FOREIGN PATENT DOCUMENTS

| CN | 104758255 | 7/2015 |
| DE | 10029770 A1 | 12/2001 |
| EP | 3144006 | 9/2017 |
| JP | 10279487 A | 10/1998 |
| WO | 2001093683 A1 | 12/2001 |

(Continued)

OTHER PUBLICATIONS

International Search Report and Written Opinion for PCT/US2015/034078, dated Aug. 31, 2015, 17 pp.
Wang, Jingxiong, et al., "Phospholipid metabolite 1-palmitoyl-lysophosphatidylcholine enhances human ether-a-go-go-related gene (HERG) K+ channel function", Circulation, 2001, vol. 104, No. 22, pp. 2645-2648.
Begum, A.N., et al., "Curcumin Structure-Function, Bioavailibility, and Efficacy in Models of Neuroinflammation and Alzheimer's Disease," The Journal of Pharmacoloby and Experimental Therapeutics, vol. 326:1, Apr. 15, 2008, pp. 196-208.

(Continued)

*Primary Examiner* — Jake M Vu
(74) *Attorney, Agent, or Firm* — Edwin S. Flores; Chalker Flores, LLP

(57) ABSTRACT

The present invention includes compositions and methods for preventing one or more cardiac channelopathies or conditions resulting from irregularities or alterations in cardiac patterns caused by an active agent or a drug in a human or animal subject comprising: an amount of a lysophosphatidyl compound adapted for oral administration effective to reduce or prevent one or more cardiac channelopathies or conditions resulting from irregularities or alterations in cardiac patterns caused by the active agent or drug. Such compositions may further comprise a monoglyceride, a free fatty acid or a combination of the foregoing, including, e.g., a eutectic mixture.

10 Claims, 9 Drawing Sheets

(56) References Cited

FOREIGN PATENT DOCUMENTS

| | | |
|---|---|---|
| WO | 2002002582 A1 | 1/2002 |
| WO | 2006131737 A2 | 12/2006 |
| WO | 2007103435 A2 | 9/2007 |
| WO | 2007129062 A1 | 11/2007 |
| WO | 2009073050 | 6/2009 |
| WO | 2013041894 | 3/2013 |
| WO | 2013166249 A1 | 11/2013 |
| WO | 2013188767 | 12/2013 |
| WO | 2015095576 A1 | 6/2015 |

OTHER PUBLICATIONS

Grama, C.N., et al., "Poly(lactide—glycolide) nanoparticles for peroral delivery of bioactives," Current Opinion in Colloid and Interface Science, London, GB, vol. 16, No. 3, Nov. 24, 2010, pp. 238-245.

Harish, G., et al., "Bioconjugates of curcumin display improved protection against glutathione depletion mediated oxidative stress in a dopaminergic neuronal cell line: Implications for Parkinson's disease," Bioorgaic & Medicinal Chemistry, vol. 18, Feb. 20, 2010, pp. 2631-2638.

Konwarh, R., et al., "Poly(ethylene glycol)-magnetic nanoparticles-curcumin trio: Directed morphogenesis and synergistic free-radical scavenging," Colloids and Surfaces B: Biointerfaces, vol. 81, Aug. 7, 2010, pp. 578-586.

Kim, K-P., et al., "Nilotinib in Patients with GIST who failed imatinib and sunitinib: importance of prior surgery on drug bioavailability," Jul. 12, 2010, Cancer Chemother. Pharmacol., vol. 68, pp. 285-291.

Kowluru, Renu A., et al., "Effects of Curcumin on Retinal Oxidative Stress and Inflammation in Diabetes," Nutrition & Metabolism, Apr. 16, 2007, 8 pages.

Kulkarni, S.K., et al., "An Overview of Curcumin in Neurological Disorders," Indian J. Pharm. Sci, Jul. 1, 2010, 72:2, pp. 149-154.

Kumar, T. Peeyush, et al., "Curcumin Modulates Dopaminergic Receptor, CREB and Phospholipase C Gene Expression in the Cerebral Cortex and Cerebellum of Streptozotocin Induced Diabetic Rats," Journal of Biomedical Science, (2010), 2:43, 11 pages.

Lamont, Benjamin J., et al., "Differential Antidiabetic Efficacy of Incretin Agonists Versus DPP-4 Inhibition in High Fat-Fed Mice," Diabetes, Jan. 2008, vol. 57, pp. 190-198.

Leung, et al., "Effective stablization of curcumin by association to plasma proteins: human serum albumin and fibronogen," Langmuir, 2009, vol. 25, Issue 10, pp. 5773-5777.

Li, Yu-Cheng, et al., "Antidepressant-Like Effects of Curcumin on Serotonergic Receptor-Coupled Ac-cAMP Pathway in Chronic Unpredictable Mild Stress of Rats," Progress in Neuro-Psychophamacoloby & Biological Psychiatry, (2009), vol. 33, pp. 435-449.

Li, Lan, et al., "Liposome-Encapsulated Curcumin in Vitro and in Vivo Effects on Proliferation, Apoptosis, Signaling, and Angiogenesis," Cancer, May 4, 2005, 104:1322-1331.

Lim, Kah Jing, et al., "A Polymeric Nanoparticle Formulation of Curcumin Inhibits Growth, Clonogenicity and Stem-Like Fraction in Malignant Brain Tumors," Cancer Biology & Therapy, Mar. 1, 2011, 11:5, pp. 464-473.

Logan-Smith, Melanie J., et al., "Curcumin, a Molecule that Inhibits the Ca2+-ATPase of Sarcoplasmic Reticulum but Increases the Rate of Accumulation of Ca2+," The Journal of Biological Chemistry, (2001), vol. 276, No. 50, pp. 46905-46911.

Mach, Claire M., et al., "Determination of Minimum Effective Dose and Optimal Dosing Schedule for Liposomal Curcumin in a Xenograft Human Pancreatic Cancer Model," (2009), Anticancer Research, 29:1895-1900.

Maciel, NR, et al., "Reduced Cardiovascular Alterations of Tarter Emetic Administered in Long-Circulating Liposomes in Rats," Toxicology Letters, 2010; 199(3):234-238.

Marino, Silvia, et al., "Sertaline in the Treatment of Depressive Disorders in Patients with Parkinson's Disease," Neurological Sciences, Nov. 2008, 29:391-395.

Matsushita, Yuichi, et al., "Activation of Peroxisome Proliferator-Activated Receptor d Inhibits Streptozotocin-Induced Diabetic Nephropathy Through Anti-Inflammatory Mechanisms in Mice," Diabetes, Mar. 2011, vol. 60, pp. 960-968.

Mayer, Lawrence D., et al., "Intravenous Pretreatment with Empty pH Liposomes Alters the Pharmacokinetics and Toxicity of Doxorubicin through in Vivo Active Drug Encapsulation," Journal of Pharmaceutical Sciences, vol. 88, No. 1, Nov. 25, 1998, pp. 96-102.

Mishra, S., et al., "The effect of curcumin (turmeric) on Alzheimer's disease: An overview," Annals of Indian Academy of Neurology, vol. 11:1, 2008, pp. 13-19.

Mukerjee, Anindita, et al., "Formulation, Characterization and Evaluation of Curcumin-Loaded PLGA Nanospheres for Cancer Therapy," (2009), Anticancer Research 29:3867-3876.

Murphy, Eric, A., et al., "Targeted Nanogels: A Versatile Platform for Drug Delivery to Tumors," Molecular Cancer Therapeutics, Apr. 25, 2011; 10:972-982.

Nam, et al., "Curcumin-Loaded PLGA Nanoparticles Coating onto Metal Stent by Electrophoretic Deposition Techniques," Bull. Korean Chem. Soc., Jan. 2007, vol. 28, No. 3, pp. 397-402.

Narala, Venkata R., et al., "Curcumin is not a Ligand for Peroxisome Proliferator-Activated Receptor-Y," Gene Therm. Mol. Biol., Apr. 1, 2009, 13(1):20-25.

Nousiainen, T., et al., "QT dispersion and late potentials during doxorubicin therapy for non-Hodgkin's lymphoma," Journal of Internal Medicine, 245, 1999, pp. 359-364.

Olansky, Leann, "Do Incretin-Based Therapies Cause Acute Pancreatitis?" Journal of Diabetes Science and Technology, Jan. 2010, vol. 4, Issue 1, pp. 228-229.

Pitman, Roger K., et al., "Conceptually Driven Pharmacologic Approaches to Acute Trauma," CNS Spectrums, Feb. 2005, vol. 10, No. 2, pp. 99-106.

Quan, Xiao-Qing, et al., "Increasing Gap Junction Coupling Reduces Transmural Dispersion of Repolarization and Prevents Torsade de Pointes in Rabbit LQT3 Model," J. Cardiovasc. Electrophysiol., vol. 18, Nov. 2007, pp. 1184-1189.

Rajeswari, A., et al., "Inhibition of monoamine oxidase-B by the polyphenolic compound, curcumin and its metabolite tetrahydrocurcumin, in a model of Parkinson's disease induced by MPTP neurodegeneration in mice," Inflammopharmacology, vol. 16, 2008, pp. 96-99.

Roberts, A.N., et al., "Molecular and Functional Characterization of Amylin, a Peptide Associated with Type 2 Diabetes Mellitus," Proc. Natl. Acad. Sci. USA, Dec. 1989, vol. 86, pp. 9662-9666.

Rosi, S., et al., "Chemokine Receptor 5 Antagonist d-Ala-Peptide T-Amide Reduces Microglia and Astrocyte Activation Within the Hippocampus in a Neuroinflammatory Rat Model of Alzheimer's Disease," Neuroscience, (2005), vol. 134, pp. 671-676.

Rui, Pan, et al., "Curcumin Improves Learning and Memory Ability and its Neuroprotective Mechanism in Mice," Chin. Med. J., (2008), vol. 121, No. 9, pp. 832-839.

Rusinek, Henry, et al., "Hippocampal Blood Flow in Normal Aging Measured with Arterial Spin Lavelin at 3T," Magnetic Resonance in Medicine, (2011), 65:128-137.

Schena, Francesco P., et al., "Pathogenetic Mechanisms of Diabetic Nephropathy," J. Am. Soc. Nephrol., (2005), 16:S30-S33.

Segman, RH., et al., "Association Between the Dopamine Transporter Gene and Posttraumatic Stress Disorder," Molecular Psychiatry, (2002), vol. 7, pp. 903-907.

Shaikh, J., et al, "Nanoparticle encapsulation improves oral bioavailability of curcumin by at least 9-fold when compared to curcumin administered with piperine as absorption enhancer," European Journal of Pharmaceutical Sciences, Elsevier, Amsterdam, NL, vol. 37, No. 3-4, Jun. 28, 2009, pp. 223-230.

Shimizu, Wataru, et al. "Effects of a K+ Channel Opener to Reduce Transmural Dispersion of Repolarization and Prevent Torsade de Pointes in LQT1, LQT2, and LQT3 Models of the Long-QT Syndrome," Circulation, 2000, 102:706-712.

(56) References Cited

OTHER PUBLICATIONS

Singh, Sonal, et al., "Long-Term Risk of Cardovascular Events with Rosiglitazone," JAMA, Sep. 12, 2007, vol. 298, No. 10, pp. 1189-1195.
Smith, Judith A., et al., "Abstract A29: Development of Liiposomal Curcumin as a New Potential Anticancer Agent," Molecular Cancer Therapeutics, Dec. 2009, vol. 8, Issue 12, Supplement 1, 1 page.
Stansfeld, Phillip, J., et al., "Drug Block of the hERG Potassium Channel: Insight From Modeling," Proteins: Structure, Function and Bioinformatics, Apr. 19, 2007, 68:568-580.
Stein, Murray B., et al., "Genetic and Environmental Influences on Trauma Exposure and Posttraumatic Stress . Disorder Symptoms: A Twin Study," Am. J. Psychiatry, Oct. 2002, vol. 159, No. 10, pp. 1675-1681.
Crouch, et al., "Clinical Relevance and Management of Drug-Related QT Interval Prolongation," Pharmacotherapy, Nov. 7, 2003, vol. 23:7, pp. 881-908.
Doherty, K., et al., "Multi-parameter in vitro toxicity testing of crizotinib, sunitinib, erlotinib, and nilotinib in human cardiomyocytes," Toxicoloty and Applied Pharmacology, Apr. 28, 2003, vol. 272, pp. 245-255.
Rodrigues, C., et al., "Derivative Spectrophotmetry as a Tool for the Determination of Drug Partition Coefficients in water/dimyristoyl-L-α-phosphatidylglycerol (DMPG) Liposomes," Biophysical Chemistry (2001); 94:97-106.
Van Dijck, P.W.M., et al., "Influence of Ca2+ and Mg2+ on the thermotropic behaviour and permeability properties of liposomes prepared from dimyristoyl phosphatidylglycerol and mixtures of dimyristoyl phosphatidylglycerol and dimyristoyl phosphatidylcholine," Biochimica et Biophysica Acta (1975); 406:465-478.
Chartrand, et al., "Potential role of the membrane in hERG channel functioning and drug-induced long QT syndrome," Biochimica et Biophysica Acta, May 25, 2010, vol. 1798, pp. 1651-1662.
Chayanupatkul, "Cirrhotic cardiomyopathy: review of pathophysiology and treatment." Hepatol Int., Jul. 2014, vol. 8, No. 3, pp. 308-315.
Dhandapani, K M., et al., "Curcumin suppresses growth and chemoresistance of human glioblastoma cells via AP-1 and NFkB transcription factors," J. Neurochem (2007) 102:522-538.
Dhule, S.S., et al., "The Combined Effect of Encapsulating Curcumin and C6 Ceramide in Liposomal Nanoparticles against Osteosarcoma," Molecular Pharmaceutics, vol. 11, No. 2, Dec. 31, 2013, pp. 417-427.
Extended European Search Report and European Search Opinion for 14864686.2 dated May 4, 2017, 8 pages.
Extended European Search Report and European Search Opinion for 16188460.6 dated Nov. 16, 2016, 12 pages.
Gilenya (Fingolimod) Full Prescribing Information, Novartis: T2016-22, Feb. 2016, 25 pp.
Gou, M., et al., "Curcumin-loaded biodegradable polymeric micelles for colon cancer therapy in vitro and in vivo," Nanoscale, vol. 3, No. 4, Oct. 2010, pp. 1558-1567.
International Search Report and Written Opinion for PCT/US2013/045898, dated Sep. 6, 2013, 12 pages.
Leung, et al., "Effective stablization of curcumin by association to plasma proteins: human serum albumin and fibronogen," Langmuir, Mar. 25, 2009, vol. 25, Issue 10, pp. 5773-5777.
National Biodiversity Authority, Secretary of Government of India, Third Party Observation for Application No. EP20110760055, submitted for observation on Jul. 20, 2017, 7 pp.
Pisarik, et al., "Reduction of free amphothericin B Acute Toxicity in Mice after intravenous administration of empty liposomes," Journal of Infectious Diseases, May 1990, 161(5), pp. 1042-1044.
Ramachandran, C., et al., "Potentiation of Etoposide and Temozolomide Cytotoxicity by Curcumin and Turmeric Force in Brain Tumer Cell Lines," Journal of Complementary and Integrative Medicine (2012), 9(1):Article 20.
Ranjan, A.P., et al., "Efficacy of Liposomal Curcumin in a Human Pancreatic Tumor Xenograft Model: Inhibition of Tumor Growth and Angiogensis," Anticancer Research, vol. 33, No. 9, Jul. 26, 2013, pp. 3603-3609.
Ravindran, J., et al., "Curcumin and Cancer Cells: How Many Ways Can Currly Kill Tumor Cells Selectively?," The AAPS Journal, vol. 11:3, Sep. 2009, pp. 495-510.
Tudor, B-A, et al., "Amphotericin B® treatment causes QT prolongation in lung transplant-pateints," Intensive Care Medicine Experimental, Oct. 2015, 3(Suppl 1):A213 poster presentation.
Vincenzi, Frank F., et al., "Citalopram-Induced Long QT Syndrome and the Mammalian Dive Reflex," Drug Saf—Case Rep, vol. 2:12, Aug. 1, 2015, 5 pp.
Yagi, Y., et al., "Analysis of Onset Mechanisms of a Sphingosine 1-Phosphate Receptor Modulator Fingolimod-Induced Atrioventricular Conduction Block and QT-Interval Prolongation," Toxicology and Applied Pharmacology, Sep. 16, 2014, 281, pp. 39-47.
Zeltser, et al., "Drug-induced atrioventricular block: prognosis after discontinuation of the culprit drug." Journal of the American College of Cardiology, Jul. 2004, vol. 44, No. 1, pp. 105-108.
Chinthalapally, et al., "Inhibition by dietary curcumin of azoxymethane-induced ornithine decarboxylase, tyrosine protein kinase, arachidonic acid metabolism and aberrant crypt foci formation in the rat colon," Carcinogensis, vol. 14, Iss. 11, Nov. 1, 1993, pp. 2219-2225.
Hasima, N., et al., "Cancer-linked targets modulated by curcumin," Int. J. Biochem. Mol. Bio., Dec. 30, 2012, vol. 3(4), pp. 328-351.
Hong, et al., "Curcumin inhibits tyrosine kinase activity of p195neu an also depletes p185neu," Clinical Cancer Research, Mar. 22, 1999, 5(7), pp. 1884-1891.
International Search Report and Written Opinion for PCT/US2017/057446, dated Dec. 29, 2017, 13 pages.
International Search Report and Written Opinion of Korean Intellectual Property Office for PCT/US2017/060936 dated Feb. 20, 2018, 13 pages.
Rawal, et al., "Paclitaxel Induced Acute ST Elevation Myocardial Infarction: A Rare Case Report," Journal of Clinical and Diagnostic Research, Oct. 2016, vol. 10(10), pp. XD01-XD02.
Shopp, G.M., et al., "Liposomes ameliorate Crizotinib- and Nilotinib-induced inhibition of the cardiac IKr channel and Qtc prolongation," Anticancer Research, 2014, vol. 34, pp. 4733-4740.
Tang, H., et al., "Curcumin Polymers as Anticancer Conjugates," Biomaterials, vol. 31, No. 27, Jun. 29, 2010, pp. 7139-7149.
Vincenzi, Frank F., et al., "Citalopram-Induced Long QT Syndrome and the Mammalian Dive Reflex," Drug Saf—Case Rep, vol. 2:12, Aug. 1, 2015, 5 pages.
Webster, G., et al., "Contemporary reviews in cardiovascular medicine, An Update on Channelopathies," Jan. 2013, vol. 127, pp. 126-140.
Who Model List of Essential Medicines, World Health Organization, Oct. 2013. pp. 1-47.
Wikipedia2, https://en.wikipedia.org/wiki/Atrioventricular_block (downloaded on Jul. 26, 2018).
Wong-Beringer, Annie, et al., "Lipid Formulations of Amphotericin B: Clinical Efficacy and Toxicities," Clinical Infectious Diseases, May 4, 1998, vol. 27, pp. 603-618.

\* cited by examiner

PROTECTIVE EFFECT OF DMPC, DMPG, DMPC/DMPG, EGPG, LYSOPG AND LYSOPC AGAINST DRUGS THAT CAUSE CHANNELOPATHIES

CROSS-REFERENCE TO RELATED APPLICATIONS

This application claims priority to U.S. Provisional Application Ser. No. 62/007,244 filed Jun. 3, 2014, U.S. Provisional Application Ser. No. 62/035,417 filed Aug. 9, 2014, U.S. Provisional Application Ser. No. 62/056,957 filed Sep. 29, 2014, U.S. Provisional Application Ser. No. 62/150,059 filed Apr. 20, 2015, the entire contents of which are incorporated herein by reference.

STATEMENT OF FEDERALLY FUNDED RESEARCH

None.

INCORPORATION-BY-REFERENCE OF MATERIALS FILED ON COMPACT DISC

None.

TECHNICAL FIELD OF THE INVENTION

The present invention relates in general to the field of drug treatment, and more particularly, to novel compositions and methods for reducing or eliminating channelopathies or conditions resulting from irregularities or alterations in cardiac patterns caused by an active agent or a drug.

BACKGROUND OF THE INVENTION

Without limiting the scope of the invention, its background is described in connection with compositions and methods for controlling the duration of repolarization of the cardiac ventricle QT in a subject.

The beating of the heart is due to precisely controlled regularly spaced waves of myocardial excitation and contraction. The electrical currents during ion-based depolarization and repolarization can be measured by electrical leads placed on the body in specific locations (the electrocardiogram) which measure electrical waves. The P-wave represents a wave of depolarization in the atrium. When the entire atria becomes depolarized, the wave returns to zero. After 0.1 seconds the ventricle is entirely depolarized resulting in the QRS complex. The three peaks are due to the way the current spreads in the ventricles. This is followed by the T-wave or repolarization of the ventricle. The QT interval measured from the beginning of the QRS complex to the end of the T wave on the standard ECG represents the duration till the completion of the repolarization phase of the cardiac myocyte (or the depolarization and repolarization of the ventricle). The duration of this interval can vary due to genetic variation, cardiac disease, electrolyte balance, envenomation, and drug treatments. Prolongation of the QT interval can result in ventricular arrhythmias and sudden death.

Drug induced long QTc Syndrome (LQTS) i.e., a prolongation of the action potential duration is a common cause of governmental mandated drug withdrawal. QTc prolongation is an unpredictable risk factor for Torsades de Pointes (TdP), a polymorphic ventricular tachycardia leading to ventricular fibrillation. Drug induced LQTS comprises about 3% of all prescriptions which when followed by TdP may constitute a lethal adverse reaction. Patients taking one or more than one QTc-prolonging drug concomitantly, have an enhanced risk of TdP. While the overall occurrence of TdP is statistically rare, it is clinically significant for the affected individual. Testing for this drug effect is a mandatory requirement prior to allowing a drug to enter clinical trials.

Common structurally diverse drugs block the human ether-a-go-go-related gene (KCNH2 or hERG) coded $K^+$ channel and the cardiac delayed-rectifier potassium current $I_K$ (KV11.1) resulting in acquired LQTS. Drug-associated increased risk of LQTS is a major drug development hurdle and many drugs have been withdrawn during pre-clinical development, assigned black box warnings following approval or withdrawn from the market. Autosomal recessive or dominant LQTS based upon 500 possible mutations in 10 different genes coding for the potassium channel has an incidence of 1:3000. Prolonged QT intervals, or risk of LQTS occur in 2.5% of the asymptomatic US population. This syndrome when expressed can lead to severe cardiac arrhythmia and sudden death in untreated patients. The probability of cardiac death in patients with asymptomatic congenital LQTS who are medicated with LQTS-inducing drugs is increased.

The majority of the acquired LTQS drug withdrawals are due to obstruction of the potassium ion channels coded by the human ether-a-go-go related gene (hERG). High concentrations of hERG blocking drugs generally induce a prolonged QTc interval and increase the probability of TdP. Up to 10% of cases of drug-induced TdP can be due to 13 major genetic mutations, 471 different mutations, and 124 polymorphisms (Chig, C 2006).

Systems and methods for detection of LQTS have been described previously. For example U.S. Patent Publication No. 2010/0004549 (Kohls et al. 2010) discloses a system and method of detecting LQTS in a patient by comparing a collected set of ECG data from the patient to a plurality of databases of collected ECG data. The plurality of databases will include a database containing previous ECGs from the patient, a known acquired LQTS characteristics database, and a known genetic LQTS characteristics database. Comparing the patient's ECG to these databases will facilitate the detection of such occurrences as changes in QT interval from success of ECGs, changes in T-wave morphology, changes in U-wave morphology, and can match known genetic patterns of LQTS. The system and method is sensitive to patient gender and ethnicity, as these factors have been shown to effect LQTS, and is furthermore capable of matching a QT duration to a database of drug effects. The system and method is also easily integrated into current ECG management systems and storage devices.

A system and method for the diagnosis and treatment of LQTS is described in U.S. Patent Publication No. 2008/0255464 (Michael, 2008). The Michael invention includes a system for diagnosing LQTS, which derives a QT/QS2 ratio from an electrical systole (QT) and a mechanical systole (QS2) to detect a prolonged QT interval in a patient's cardiac cycle. A processor acquires the systoles from a microphone and chest electrodes, calculates the QT/QS2 ratio, and outputs the result to a display. The processor may compare the QT/QS2 ratio to a threshold value stored in memory for diagnosing LQTS in the patient. A user interface provides for programming, set-up, and customizing the display. A mode selector allows the system to operate alternatively as a phonocardiograph, a 12 lead electrocardiograph, or a machine for diagnosing LQTS. A related method for diagnosing cardiac disorders such as LQTS includes measuring QT and QS2 during a same cardiac cycle, calculating a QT/QS2 ratio, and comparing the result to a threshold value derived from empirical data. The method may include measuring systoles both at rest and during exercise, and may be used for drug efficacy, dosage optimization, and acquired LQTS causality tests.

A method for the treatment of cardiac arrhythmias is provided in U.S. Patent Publication No. 2007/0048284 (Donahue and Marban, 2007). The method includes administering an amount of at least one polynucleotide that modulates an electrical property of the heart. The polynucleotides of the invention may also be used with a microdelivery vehicle such as cationic liposomes and adenoviral vectors.

Methods, compositions, dosing regimes, and routes of administration for the treatment or prevention of arrhythmias have been described by Fedida et al. (2010) in U.S. Patent Publication No. 2001/00120890. In the Fedida invention, early after depolarizations and prolongation of QT interval may be reduced or eliminated by administering ion channel modulating compounds to a subject in need thereof. The ion channel modulating compounds may be cycloalkylamine ether compounds, particularly cyclohexylamine ether compounds. Also described are compositions of ion channel modulating compounds and drugs which induce early after depolarizations, prolongation of QT interval and/or Torsades de Pointes. The Fedida invention also discloses antioxidants which may be provided in combination with the ion channel modulating compounds, non-limiting examples of the antioxidants include vitamin C, vitamin E, beta-carotene, lutein, lycopene, vitamin B2, coenzyme Q10, cysteine as well as herbs, such as bilberry, turmeric (curcumin), grape seed or pine bark extracts, and ginkgo.

SUMMARY OF THE INVENTION

In one embodiment, the present invention provides a composition comprising an amount of a lysophaspatidyl compound of the general formula I (as described below). In one aspect, the composition is used for preventing or treating one or more cardiac channelopathies or conditions resulting from irregularities or alterations in cardiac patterns caused by an active agent or a drug, when the active agent or drug is administered to a human or animal subject, the composition effective to reduce or prevent the one or more cardiac channelopathies or conditions resulting from irregularities or alterations in cardiac patterns caused by the active agent or drug. In another aspect, the composition is used for preventing or treating diseases with an active agent or drug, wherein the active agent or drug causes one or more adverse reactions arising from administration of the active agent or drug in a human, the composition effective to reduce or prevent the one or more adverse reactions arising from administration of the active agent or drug.

In another aspect, the composition further comprises at least one of 1-Myristoyl-2-Hydroxy-sn-Glycero-3-Phosphocholine (DMPC), 12-Mysteroyl-2-Hydroxy-sn-Glycero-3-[Phospho-rac-(glycerol)] (DMPG), a monoglyceride of the general formula II (as defined below), a free fatty acid of the general formula III (as defined below), or a combination of the foregoing. In another aspect, the composition further comprises at least one of a monoglyceride of the general formula II, a free fatty acid of the general formula III, or a combination of the foregoing. In one aspect, the lipids are selected from at least one of 10:0 LysoPG, 12:0 LysoPG, 14:0 LysoPG, 14:0 EGPG, 16:0 LysoPG, or 18:0 LysoPG. In another aspect, the composition forms a eutectic mixture.

In another aspect, the cardiac channelopathy or the condition resulting from the irregularity or alteration in the cardiac pattern is inhibition of an ion channel responsible for the delayed-rectifier $K^+$ current in the heart, polymorphic ventricular tachycardia, prolongation of the QTc, LQT2, LQTS, or torsades de pointes. In another aspect, the composition is used for the treatment or prevention of prolongation of the $I_{Kr}$ channel inhibition or QT prolongation induced by administration of the active agent or drug used in the treatment of cardiac, allergic, or cancer related diseases. In another aspect, the active agent drug is provided enterally, parenterally, intravenously, intraperitoneally, or orally. In another aspect, the active agent drug is provided in a liposomes and comprises a lipid or a phospholipid wall, wherein the lipids or the phospholipids are selected from the group consisting of phosphatidylcholine (lecithin), lysolecithin, lysophosphatidylethanol-amine, phosphatidylserine, phosphatidylinositol, sphingomyelin, phosphatidylethanolamine (cephalin), cardiolipin, phosphatidic acid, cerebrosides, dicetylphosphate, phosphatidylcholine, and dipalmitoyl-phosphatidylglycerol, stearylamine, dodecylamine, hexadecyl-amine, acetyl palmitate, glycerol ricinoleate, hexadecyl sterate, isopropyl myristate, amphoteric acrylic polymers, fatty acid, fatty acid amides, cholesterol, cholesterol ester, diacylglycerol, and diacylglycerolsuccinate. In another aspect, the drug is selected from Albuterol (salbutamol), Alfuzosin, Amantadine, Amiodarone, Amisulpride, Amitriptyline, Amoxapine, Amphetamine, Anagrelide, Apomorphine, Arformoterol, Aripiprazole, Arsenic trioxide, Astemizole, Atazanavir, Atomoxetine, Azithromycin, Bedaquiline, Bepridil, Bortezomib, Bosutinib, Chloral hydrate, Chloroquine, Chlorpromazine, Ciprofloxacin, Cisapride, Citalopram, Clarithromycin, Clomipramine, Clozapine, Cocaine, Crizotinib, Dabrafenib, Dasatinib, Desipramine, Dexmedetomidine, Dexmethylphenidate, Dextroamphetamine (d-Amphetamine), Dihydroartemisinin and piperaquine, Diphenhydramine, Disopyramide, Dobutamine, Dofetilide, Dolasetron, Domperidone, Dopamine, Doxepin, Dronedarone, Droperidol, Ephedrine, Epinephrine (Adrenaline), Eribulin, Erythromycin, Escitalopram, Famotidine, Felbamate, Fenfluramine, Formoterol, Foscarnet, Fosphenytoin, Fluconazole, Fluoxetine, Furosemide (Frusemide), Galantamine, Gatifloxacin, Gemifloxacin, Granisetron, Halofantrine, Haloperidol, Hydrochlorothiazide, Ibutilide, Iloperidone, Imipramine (melipramine), Indapamide, Isoproterenol, Isradipine, Itraconazole, Ivabradine, Ketoconazole, Lapatinib, Levalbuterol (levsalbutamol), Levofloxacin, Levomethadyl, Lisdexamfetamine, Lithium, Mesoridazine, Metaproterenol, Methadone, Methamphetamine (methamfetamine), Methylphenidate, Midodrine, Mifepristone, Mirabegron, Mirtazapine, Moexipril/HCTZ, Moxifloxacin, Nelfinavir, Nicardipine, Nilotinib, Norepinephrine (noradrenaline), Norfloxacin, Nortriptyline, Ofloxacin, Olanzapine, Ondansetron, Oxytocin, Paliperidone, Paroxetine, Pasireotide, Pazopanib, Pentamidine, Perflutren lipid microspheres, Phentermine, Phenylephrine, Phenylpropanolamine, Pimozide, Posaconazole, Probucol, Procainamide, Promethazine, Protriptyline, Pseudoephedrine, Quetiapine, Quinidine, Quinine sulfate, Ranolazine, Rilpivirine, Risperidone, Ritodrine, Ritonavir, Roxithromycin, Salmeterol, Saquinavir, Sertindole, Sertraline, Sevoflurane, Sibutramine, Solifenacin, Sorafenib, Sotalol, Sparfloxacin, Sulpiride, Sunitinib, Tacrolimus, Tamoxifen, Telaprevir, Telavancin, Telithromycin, Terbutaline, Terfenadine, Tetrabenazine, Thioridazine, Tizanidine, Tolterodine, Toremifene, Trazodone, Trimethoprim-Sulfa, Trimipramine, Vandetanib, Vardenafil, Vemurafenib, Venlafaxine, Voriconazole, Vorinostat, or Ziprasidone. In another aspect, the active agent drug is selected from at least one of Crizotinib, Nilotinib, Terfenadine, Astemizole, Gripafloxacin, Terodilene, Droperidole, Lidoflazine, Levomethadyl, Sertindoyle or Cisapride. In one embodiment of the foregoing, the composition is adapted for oral administration. In one aspect, the lipids are selected from at least one of 10:0 LysoPG, 12:0 LysoPG, 14:0 LysoPG, 14:0 EGPG, 16:0 LysoPG, or 18:0 LysoPG.

In another aspect, the lysophosphatidyl compound is selected from at least one of lauroyl-lysophosphatidyl compounds, myristoyllysophosphatidyl compounds, palmitoyl-lysophosphatidyl compounds, stearoyl-lysophosphatidyl compounds, arachidoyl-lysophosphatidyl compounds, oleoyl-lysophosphatidyl compounds, linoleoyllysophosphatidyl compounds, linolenoyl-lysophosphatidyl compounds or erucoyl lysophosphatidyl compounds. In another aspect, the composition further comprises a free fatty acid and a monoglyceride (for example a fatty acid of the general formula III and a monoglyceride of the general formula II). In another aspect, the composition forms a eutectic mixture. In another aspect, the free fatty acid and monoglyceride are present in the composition in a molar ratio of between about 2:1, 1:1, and 1:2. In another aspect, the free fatty acid and monoglyceride comprise from about 70 mole to 99 mole percent of the composition, with the lysophosphatidyl compound comprising from about 30 mole percent to 1 mole percent of the composition. In another aspect, the ratios of the components of the composition are 1:4:2, a 1:3:3, a 2:4:2, or a 1:2:4 mole percent lysophosphatidyl compound:monoglyceride:free fatty acid. In another aspect, the composition is a eutectic mixture comprising LysoPG:myristoyl monoglyceride:myristic fatty acid. In another aspect, the composition has a ratio of phospholipids to active agent of from 15:1 to 0.03:1 (for example, 9:1, 3:1, 1:1, 0.3:1, and 0.1:1).

In one embodiment, the present invention includes a method for preventing or treating one or more cardiac channelopathies, irregularities or alterations in cardiac patterns, IKr channel inhibition or QT prolongation, in a human or animal subject caused by an active agent or drug, wherein the active agent or drug is used to treat a disease in a human or animal subject comprising the steps of: administering to the human or animal subject an amount of a composition comprising a lysophosphatidyl compound of the general formula I adapted for oral administration effective to reduce or prevent the at least one of cardiac channelopathies, irregularities or alterations in cardiac patterns, IKr channel inhibition, or QT prolongation caused by the active agent or drug; and an effective amount of the active agent or drug sufficient to treat the disease, wherein the orally provided composition comprising a lysophosphatidyl compound reduces or eliminates the at least one cardiac channelopathies, irregularities or alterations in cardiac patterns, IKr channel inhibition or QT prolongation. In one aspect, the lipids are selected from at least one of 10:0 LysoPG, 12:0 LysoPG, 14:0 LysoPG, 14:0 EGPG, 16:0 LysoPG, or 18:0 LysoPG. In another aspect, the composition further comprises a free fatty acid and a monoglyceride (for example a fatty acid of the general formula III and a monoglyceride of the general formula II). In another aspect, the composition is formed into a eutectic mixture. In another aspect, the free fatty acid and a monoglyceride are present in the composition in a molar ratio of between about 2:1, 1:1, and 1:2. In another aspect, the free fatty acid and monoglyceride comprise from about 70 mole to 99 mole percent of the composition, with the lysophosphatidyl compound comprising from about 30 mole percent to 1 mole percent of the composition. In another aspect, the ratios of the components of the composition are 1:4:2, 1:3:3, 2:4:2, or 1:2:4 mole percent lysophosphatidyl compound:monoglyceride:free fatty acid. In another aspect, the composition is a eutectic mixture comprising LysoPG:myristoyl monoglyceride:myristic fatty acid. In another aspect, the composition has a ratio of phospholipids to active agent of from 15:1 to 0.03:1 (for example, 9:1, 3:1, 1:1, 0.3:1, and 0.1:1).

In one embodiment, the present invention includes a method for preventing or treating one or more adverse reactions arising from administration of a therapeutically active agent or a drug in a human or animal subject comprising the steps of: administering to the human or animal subject an amount of an amount of a composition comprising a lysophosphatidyl compound of the general formula I. In one aspect, the lipids are selected from at least one of 10:0 LysoPG, 12:0 LysoPG, 14:0 LysoPG, 14:0 EGPG, 16:0 LysoPG, or 18:0 LysoPG. In another aspect, the composition further comprises a free fatty acid and a monoglyceride (for example a fatty acid of the general formula III and a monoglyceride of the general formula II). In another aspect, the composition is formed into a eutectic mixture. In another aspect, the free fatty acid and a monoglyceride are present in the composition in the composition in a molar ratio of between about 2:1, 1:1, and 1:2. In another aspect, the free fatty acid and monoglyceride comprise from about 70 mole to 99 mole percent of the composition, with the lysophosphatidyl compound comprising from about 30 mole percent to 1 mole percent of the composition. In another aspect, the ratios of the components of the composition are 1:4:2, 1:3:3, 2:4:2, or 1:2:4 mole percent lysophosphatidyl compound:monoglyceride:free fatty acid. In another aspect, the composition is a eutectic mixture comprising LysoPG:myristoyl monoglyceride:myristic fatty acid. In another aspect, the composition has a ratio of phospholipids to active agent of from 15:1 to 0.03:1 (for example, 9:1, 3:1, 1:1, 0.3:1, and 0.1:1). In one embodiment, the present invention includes a method for preventing or treating one or more cardiac channelopathies, irregularities or alterations in cardiac patterns, $I_{Kr}$ channel inhibition or QT prolongation, in a human or animal subject caused by an active agent or drug, wherein the active agent or drug is used to treat a disease in a human or animal subject comprising the steps of: administering to the human or animal subject an amount of a composition comprising a lysophosphatidyl compound of the general formula I adapted for oral administration effective to reduce or prevent the at least one of cardiac channelopathies, irregularities or alterations in cardiac patterns, $I_{Kr}$ channel inhibition, or QT prolongation caused by the active agent or drug; and an effective amount of the active agent or drug sufficient to treat the disease, wherein the orally provided composition comprising a lysophosphatidyl compound reduces or eliminates the at least one cardiac channelopathies, irregularities or alterations in cardiac patterns, $I_{Kr}$ channel inhibition or QT prolongation. In one aspect, the lipids are selected from at least one of 10:0 LysoPG, 12:0 LysoPG, 14:0 LysoPG, 14:0 EGPG, 16:0 LysoPG, or 18:0 LysoPG. In one aspect, the active agent is selected from at least one of an adrenergic agent; adrenocortical steroid; adrenocortical suppressant; aldosterone antagonist; analgesic; anesthetic; anti-acne agent; anti-adrenergic; anti-allergic; anti-amebic; anti-anemic; anti-anginal; anti-arthritic; anti-asthmatic; anti-atherosclerotic; antibacterial; anticholinergic; anticoagulant; anticonvulsant; antidepressant; antidiabetic; antidiarrheal; antidiuretic; anti-emetic; anti-epileptic; antifibrinolytic; antifungal; antihemorrhagic; antihistamine; antihyperlipidemia; antihypertensive; antihypotensive; anti-infective; anti-inflammatory; antimicrobial; antimigraine; antimitotic; antimycotic, antinauseant, antineoplastic, antineutropenic, antiparasitic; antiproliferative; antipsychotic; antirheumatic; antiseborrheic; antisecretory; antispasmodic; antithrombotic; anti-ulcerative; antiviral; appetite suppressant; blood glucose regulator; bone resorption inhibitor; bronchodilator; cardiovascular agent; cholinergic; depressant; diagnostic aid; diuretic; dopaminergic agent; estrogen receptor agonist; fibrinolytic; gastric acid supressant; gastrointestinal motility effector; glucocorticoid; hemostatic; histamine H2 receptor antagonists; hypocholesterolemic; hypoglycemic; hypolipidemic; hypotensive; immunomodulator; immunostimulant; immunosuppressant; LHRH agonist; mood regulator; nasal decongestant; neuromuscular blocking agent; neuroprotective; NMDA antagonist; non-hormonal sterol derivative; psychotropic; sedative; sedative-hypnotic; selective adenosine A1 antagonist; serotonin antagonist; serotonin inhibitor; serotonin receptor antagonist; steroid; tranquilizer; unstable angina agent; vasoconstrictor; and vasodilator.

In another aspect, the composition further comprises a free fatty acid and a monoglyceride (for example a fatty acid of the general formula III and a monoglyceride of the general formula II). In another aspect, the composition is formed into a eutectic mixture. In another aspect, the free fatty acid and a monoglyceride are present in the composition in the composition in a molar ratio of between about 2:1, 1:1, and 1:2. In another aspect, the free fatty acid and monoglyceride comprise from about 70 mole to 99 mole percent of the composition, with the lysophosphatidyl compound comprising from about 30 mole percent to 1 mole percent of the composition. In another aspect, the ratios of the components of the composition are 1:4:2, 1:3:3, 2:4:2, or 1:2:4 mole percent lysophosphatidyl compound:monoglyceride:free fatty acid. In another aspect, the composition is a eutectic mixture comprising LysoPG:myristoyl monoglyceride:myristic fatty acid. In another aspect, the composition has a ratio of phospholipids to active agent of from 15:1 to 0.03:1 (for example, 9:1, 3:1, 1:1, 0.3:1, and 0.1:1). In one embodiment, the present invention includes a method for preventing or treating one or more adverse reactions arising from administration of a therapeutically active agent or a drug in a human or animal subject comprising the steps of: administering to the human or animal subject an amount of composition comprising a lysophosphatidyl compound of the general formula I. In one embodiment, the present invention includes a method for preventing or treating at least one of $I_{Kr}$ channel inhibition or QT prolongation arising from administration of an active agent that causes a drug-induced channelopathy in a human or animal subject comprising the steps of: identifying the human or animal subject in need of prevention or treatment of a disease treatable with an active agent that causes a drug-induced channelopathy; and an amount of composition comprising a lysophosphatidyl compound of the general formula I adapted for oral administration effective to reduce or prevent one or more cardiac channelopathies or conditions resulting from irregularities or alterations in cardiac patterns caused by the active agent; and administering to the human or animal subject a therapeutically effective amount of an active agent that causes a drug-induced channelopathy, wherein the orally delivered composition comprising the lysophosphatidyl compound reduces or eliminates the channelopathy induced by the therapeutically active agent. In one aspect, the active agent has previously failed a clinical trial due to drug-induced IKr channel inhibition or QT prolongation. In another aspect, the method further comprises the step of identifying a drug in a clinical trial that failed or has limited clinical use due to drug-induced IKr channel inhibition or QT prolongation side-effects. In another aspect, the drug is selected from Albuterol (salbutamol), Alfuzosin, Amantadine, Amiodarone, Amisulpride, Amitriptyline, Amoxapine, Amphetamine, Anagrelide, Apomorphine, Arformoterol, Aripiprazole, Arsenic trioxide, Astemizole, Atazanavir, Atomoxetine, Azithromycin, Bedaquiline, Bepridil, Bortezomib, Bosutinib, Chloral hydrate, Chloroquine, Chlorpromazine, Ciprofloxacin, Cisapride, Citalopram, Clarithromycin, Clomipramine, Clozapine, Cocaine, Crizotinib, Dabrafenib, Dasatinib, Desipramine, Dexmedetomidine, Dexmethylphenidate, Dextroamphetamine (d-Amphetamine), Dihydroartemisinin+piperaquine, Diphenhydramine, Disopyramide, Dobutamine, Dofetilide, Dolasetron, Domperidone, Dopamine, Doxepin, Dronedarone, Droperidol, Ephedrine, Epinephrine (Adrenaline), Eribulin, Erythromycin, Escitalopram, Famotidine, Felbamate, Fenfluramine, Fingolimod, Flecainide, Fluconazole, Fluoxetine, Formoterol, Foscarnet, Fosphenytoin, Furosemide (Frusemide), Galantamine, Gatifloxacin, Gemifloxacin, Granisetron, Halofantrine, Haloperidol, Hydrochlorothiazide, Ibutilide, Iloperidone, Imipramine (melipramine), Indapamide, Isoproterenol, Isradipine, Itraconazole, Ivabradine, Ketoconazole, Lapatinib, Levalbuterol (levsalbutamol), Levofloxacin, Levomethadyl, Lisdexamfetamine, Lithium, Mesoridazine, Metaproterenol, Methadone, Methamphetamine (methamfetamine), Methylphenidate, Midodrine, Mifepristone, Mirabegron, Mirtazapine, Moexipril/HCTZ, Moxifloxacin, Nelfinavir, Nicardipine, Nilotinib, Norepinephrine (noradrenaline), Norfloxacin, Nortriptyline, Ofloxacin, Olanzapine, Ondansetron, Oxytocin, Paliperidone, Paroxetine, Pasireotide, Pazopanib, Pentamidine, Perflutren lipid microspheres, Phentermine, Phenylephrine, Phenylpropanolamine, Pimozide, Posaconazole, Probucol, Procainamide, Promethazine, Protriptyline, Pseudoephedrine, Quetiapine, Quinidine, Quinine sulfate, Ranolazine, Rilpivirine, Risperidone, Ritodrine, Ritonavir, Roxithromycin, Salmeterol, Saquinavir, Sertindole, Sertraline, Sevoflurane, Sibutramine, Solifenacin, Sorafenib, Sotalol, Sparfloxacin, Sulpiride, Sunitinib, Tacrolimus, Tamoxifen, Telaprevir, Telavancin, Telithromycin, Terbutaline, Terfenadine, Tetrabenazine, Thioridazine, Tizanidine, Tolterodine, Toremifene, Trazodone, Trimethoprim-Sulfa, Trimipramine, Vandetanib, Vardenafil, Vemurafenib, Venlafaxine, Voriconazole, Vorinostat, or Ziprasidone. In one aspect, the lipids are selected from at least one of 10:0 LysoPG, 12:0 LysoPG, 14:0 LysoPG, 14:0 EGPG, 16:0 LysoPG, or 18:0 LysoPG.

In one embodiment, the present invention includes a method of evaluating a candidate drug, wherein the candidate drug causes a channelopathy, the method comprising: (a) administering an amount of an oral lysophosphatidyl compound or composition as described above and a candidate drug to a first subset of the patients, and a placebo (with or without the candidate drug) to a second subset of the patients, wherein the oral lysophosphatidyl compound or composition is provided in an amount effective to reduce or prevent one or more cardiac channelopathies or conditions resulting from irregularities or alterations in cardiac patterns caused by the candidate drug; (b) measuring the level of channelopathy from the first and second set of patients; and (c) determining if the combination of the oral lysophosphatidyl compound or composition and the candidate drug reduce the drug-induced channelopathy that is statistically significant as compared to any reduction occurring in the subset of patients that took the placebo or to the known drug-induced channelopathy, wherein a statistically significant reduction indicates that the combination of the oral lysophosphatidyl compound and the candidate drug is useful in treating a disease state while also reducing or eliminating the drug-induced channelopathy. In another aspect, the drug has previously failed a clinical trial due to a drug-induced channelopathy, IKr channel inhibition or QT prolongation. In another aspect, the drug has been withdrawn from the marketplace due to a drug-induced channelopathy, IKr channel inhibition or QT prolongation. In another aspect, the method further comprises the step of repeating steps (a) to (c) after a period of time. In another aspect, the drug is selected from Albuterol (salbutamol), Alfuzosin, Amantadine, Amiodarone, Amisulpride, Amitriptyline, Amoxapine, Amphetamine, Anagrelide, Apomorphine, Arformoterol, Aripiprazole, Arsenic trioxide, Astemizole, Atazanavir, Atomoxetine, Azithromycin, Bedaquiline, Bepridil, Bortezomib, Bosutinib, Chloral hydrate, Chloroquine, Chlorpromazine, Ciprofloxacin, Cisapride, Citalopram, Clarithromycin, Clomipramine, Clozapine, Cocaine, Crizotinib, Dabrafenib, Dasatinib, Desipramine, Dexmedetomidine, Dexmethylphenidate, Dextroamphetamine (d-Amphetamine), Dihydroartemisinin+piperaquine, Diphenhydramine, Disopyramide, Dobutamine, Dofetilide, Dolasetron, Domperidone, Dopamine, Doxepin, Dronedarone, Droperidol, Ephedrine, Epinephrine (Adrenaline), Eribulin, Erythromycin, Escitalopram, Famotidine, Felbamate, Fenfluramine, Fingolimod, Flecainide, Fluconazole, Fluoxetine, Formoterol, Foscarnet, Fosphenytoin, Furosemide (Frusemide), Galantamine, Gatifloxacin, Gemifloxacin, Granisetron, Halofantrine, Haloperidol, Hydrochlorothiazide, Ibutilide, Iloperidone, Imipramine (melipramine), Indapamide, Isoproterenol, Isradipine, Itraconazole, Ivabradine, Ketoconazole, Lapatinib, Levalbuterol (levsalbutamol), Levofloxacin, Levomethadyl, Lisdexamfetamine, Lithium, Mesoridazine, Metaproterenol, Methadone, Methamphetamine (methamfetamine), Methylphenidate, Midodrine, Mifepristone, Mirabegron, Mirtazapine, Moexipril/HCTZ, Moxifloxacin, Nelfinavir, Nicardipine, Nilotinib, Norepinephrine (noradrenaline), Norfloxacin, Nortriptyline, Ofloxacin, Olanzapine, Ondansetron, Oxytocin, Paliperidone, Paroxetine, Pasireotide, Pazopanib, Pentamidine, Perflutren lipid microspheres, Phentermine, Phenylephrine, Phenylpropanolamine, Pimozide, Posaconazole, Probucol, Procainamide, Promethazine, Protriptyline, Pseudoephedrine, Quetiapine, Quinidine, Quinine sulfate, Ranolazine, Rilpivirine, Risperidone, Ritodrine, Ritonavir, Roxithromycin, Salmeterol, Saquinavir, Sertindole, Sertraline, Sevoflurane, Sibutramine, Solifenacin, Sorafenib, Sotalol, Sparfloxacin, Sulpiride, Sunitinib, Tacrolimus, Tamoxifen, Telaprevir, Telavancin, Telithromycin, Terbutaline, Terfenadine, Tetrabenazine, Thioridazine, Tizanidine, Tolterodine, Toremifene, Trazodone, Trimethoprim-Sulfa, Trimipramine, Vandetanib, Vardenafil, Vemurafenib, Venlafaxine, Voriconazole, Vorinostat, or Ziprasidone. In one aspect, the lipids are selected from at least one of 10:0 LysoPG, 12:0 LysoPG, 14:0 LysoPG, 14:0 EGPG, 16:0 LysoPG, or 18:0 LysoPG.

FIG. 15 shows the cytokine data (IL-6 and TNF-a) with empty liposomes compared with EU8120.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
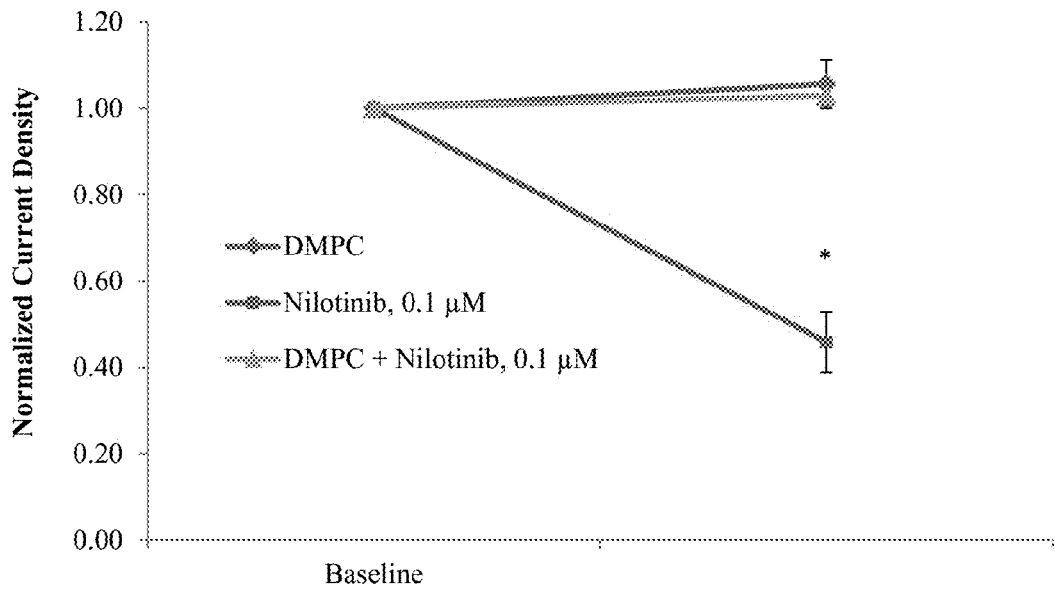
FIG. 1 is a graph that shows the effect of DMPC, DMPC+Nilotinib and Nilotinib on hERG current density from transfected HEK 293 cells.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention provides a composition comprising an amount of a lysophaspatidyl compound of the general formula I.

In one embodiment, the composition is used for preventing or treating one or more cardiac channelopathies or conditions resulting from irregularities or alterations in cardiac patterns caused by an active agent or a drug, when the active agent or drug is administered to a human or animal subject, the composition being effective to reduce or prevent the one or more cardiac channelopathies or conditions resulting from irregularities or alterations in cardiac patterns caused by the active agent or drug.

In another embodiment, the composition is used for preventing or treating diseases treatable with an active agent or drug, wherein the active agent or drug causes one or more adverse reactions arising from administration of the active agent or drug in a human, the composition effective to reduce or prevent the one or more adverse reactions arising from administration of the active agent or drug. In such an embodiment, the adverse reaction arising from the administration of the drug or active agent includes, but not limited to, cardiac channelopathies, IKr channel inhibition or QT prolongation.

In one aspect of the foregoing composition, the lysophaspatidyl compound has the general formula I:

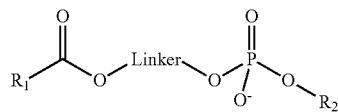

wherein, $R_1$ is a saturated or unsaturated carbon chain;

$R_2$ is H, acyl, alkyl, aryl, alkenes, alkynes or amino acid; and,

Linker is a linking portion.

In one embodiment, the $R_1$ group is a saturated carbon chain. In another embodiment, the carbon chain is an unsaturated carbon chain; in one aspect, when $R_1$ is an unsaturated carbon chain, the carbon chain may contain from 1 to 6, from 1 to 4 or from 1 to 3 double bonds. In another embodiment, the $R_1$ group is a carbon chain up to 5 carbons in length, a carbon chain from 6 to 12 carbons in length, a carbon chain from 13-21 carbons in length and a carbon chain greater than 22 carbons in length; in a particular aspect, the carbon chain is from 13 to 21 carbons in length. Such carbon chain, regardless of the length, includes both even and odd chain lengths. In another embodiment, the $R_1$ group has a carbon chain length of 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55 or more carbons, which are saturated or unsaturated. In another embodiment, the $R_1$ group has a carbon chain length of 3, 4, 5, 6, 7, 8, 9, 10, 11, 12, 13, 14, 15, 16, 17, 18, 19, 20 or 21 carbons, which are saturated or unsaturated. In another embodiment, the $R_1$ group on has a carbon chain length of 10, 11, 12, 13, 14, 15, 16, 17, 18, 19, 20 or 21 carbons, which are saturated or unsaturated. In another embodiment, the $R_1$ group has a carbon chain length of 12, 13, 14, 15 or 16, carbons, which are saturated or unsaturated. In another embodiment, the $R_1$ group has a carbon chain length of 14 carbons, which is saturated.

Non-limiting exemplary lysophosphatidyl compounds for use with the present invention include lauroyl-lysophosphatidyl compounds, myristoyllysophosphatidyl compounds, palmitoyl-lysophosphatidyl compounds, stearoyl-lysophosphatidyl compounds, arachidoyl-lysophosphatidyl compounds, oleoyl-lysophosphatidyl compounds, linoleoyllysophosphatidyl compounds, linolenoyl-lysophosphatidyl compounds and erucoyl lysophosphatidyl compounds.

In one embodiment, the $R_2$ group is a substituted alkyl chain. In embodiment, the $R_2$ group is a substituted alkyl chain, wherein the alkyl chain is substituted by one or more hydroxy groups, substituted N groups or $NH_3$ groups. In another embodiment, the $R_2$ group is —$(CH_2)_2$—$(N)(CH_3)_3$, —$CH_2$—$CH(OH)$—$CH_2$—$CH(OH)$ or $(CH_2)_2$—$NH_3$.

In one embodiment, the $R_2$ group is an amino acid moiety of the formula —$CH_2$—$CH(R_3)$—$C$=$O(O^-)$, where $R_3$ is a side chain of a naturally occurring or non-naturally occurring amino acid. In a particular embodiment, $R_3$ is —$NH_3$.

In one aspect of the foregoing, the linker is a non-immunogenic, hydrophilic polymer. Representative hydrophilic polymers include, but are not limited to, linear or branched poly(dextran), linear or branched (poly(cellulose), linear and branched poly(ethylene glycol), linear and branched poly(alkylene oxide), linear and branched poly(vinyl pyrrolidone), linear and branched poly(vinyl alcohol), linear and branched polyoxazoline, linear and branched poly(acryloylmorpholine), and derivatives thereof. In one aspect of the foregoing, the linker is linear poly(ethylene glycol). In any of the foregoing, the repleating units of the polymer may vary from 1 to 50, more particularly from 1 to 25, from 1 to 15 or from 2 to 8.

In one aspect of the foregoing, the linker is a glycerol moiety or an alkyl chain and the lysophosphatidyl compound has a structure of the general formula IA or IB.

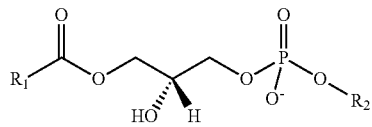

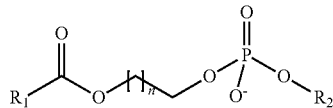

Wherein $R_1$ and $R_2$ are as defined above and n is from 1 to 20, 1 to 10 or 1 to 6. In a particular aspect, n is 1 to 6. Compounds of the formula 1B have the advantage that the lysophosphatidyl compounds are hydrolyzable at a slower rate as compared to compounds of the formula IA when administered to subjects, including human subjects.

In another aspect, the lysophosphatidyl compound is a lysophosphatidylglycerol. In another aspect, the lysophosphatidylglycerol is 1-myristoyl-2-hydroxy-sn-glycero-3-phospho-(1'-rac-glycerol). Representative lysophosphatidylglycerol compounds include those shown below IC to IE, wherein $R_1$ and n are as defined above.

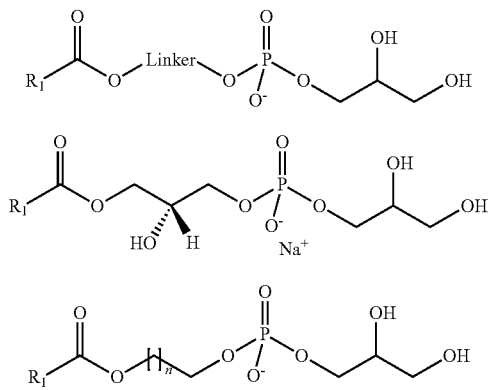

In a particular embodiment, R₁ is a saturated carbon chain of 13 carbons in length and the compound has the structure IJ:

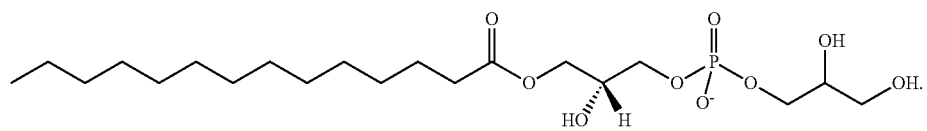

In another aspect, the lysophosphatidyl compound is a lysophosphatidylcholine. In another aspect, the lysophosphatidylcholine is 1-myristoyl-2-hydroxy-sn-glycero-3-phosphocholine. Representative lysophosphatidylcholine compounds include those shown below IF to IH, wherein R₁ and n are as defined above.

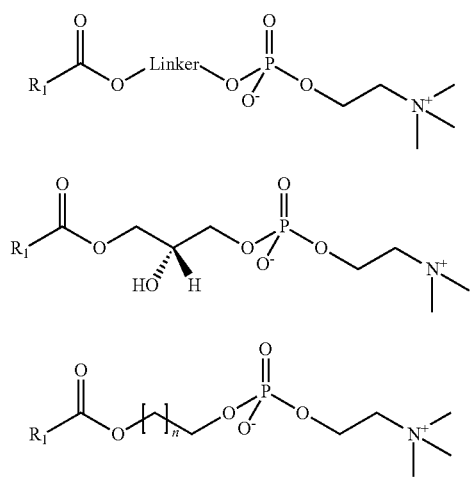

In a particular embodiment, R₁ is a saturated carbon chain of 13 carbons in length and the compound has the structure IK

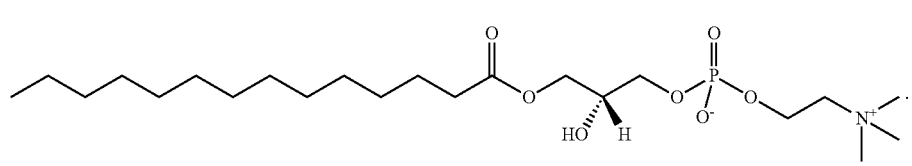

In another embodiment, the composition further comprises at least one of 1-Myristoyl-2-Hydroxy-sn-Glycero-3-Phosphocholine (DMPC), 12-Mysteroyl-2-Hydroxy-sn-Glycero-3-[Phospho-rac-(glycerol)] (DMPG), a monoglyceride of the general formula II, a free fatty acid of the general formula III, or a combination of the foregoing. In another embodiment, the composition further comprises at least one of a monoglyceride of the general formula II, a free fatty acid of the general formula III, or a combination of the foregoing.

Monoglycerides for use in the present disclosure have the general formula II

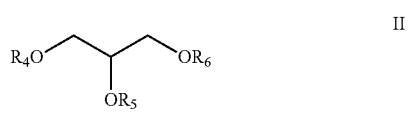

wherein: one of $R_4$, $R_5$ and $R_6$ is —C(O)—$R_7$ and the remaining are each independently selected from H or $R_8$,

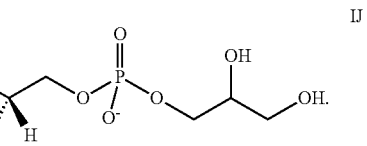

wherein $R_7$ is a saturated or unsaturated carbon chain and $R_8$ is saturated or unsaturated carbon chain from 1 to 10 carbons in length.

In one embodiment, the $R_7$ group is a saturated carbon chain. In another embodiment, the $R_7$ group is an unsaturated carbon chain; when $R_7$ is an unsaturated carbon chain, the carbon chain may contain from 1 to 6, from 1 to 4 or from 1 to 3 double bonds. In another embodiment, the $R_7$ group is a carbon chain up to 5 carbons in length, a carbon chain from 6 to 12 carbons in length, a carbon chain from 13-21 carbons in length and a carbon chain greater than 22 carbons in length; in a particular embodiment, the carbon chain is from 13 to 21 carbons in length. Such carbon chain, regardless of the length, includes both even and odd chain lengths. In another embodiment, the $R_7$ group has a carbon chain length of 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55 or more carbons, which are saturated or unsaturated. In another embodiment, the $R_7$ group has a carbon chain length of 3, 4, 5, 6, 7, 8, 9, 10, 11, 12, 13, 14, 15, 16, 17, 18, 19, 20 or 21 carbons, which are saturated or unsaturated. In another embodiment, the $R_7$ group has a carbon chain length of 10, 11, 12, 13, 14, 15, 16, 17, 18, 19, 20 or 21 carbons, which are saturated or unsaturated. In another embodiment, the $R_7$ group has a carbon chain length of 12, 13, 14, 15 or 16, carbons, which are saturated or unsaturated. In another embodiment, the $R_7$ group has a carbon chain length of 14 carbons, which is saturated.

Monoglycerides are a glycerol molecule wherein the glycerol molecule has formed an ester bond with exactly one fatty acid molecule. Monoglycerides are also referred to as acylglycerol and monoacylglycerol. A monoacylglycerol is either a 1-monoacylglycerol or a 2-monoacylglycerol, depending on the position of the ester bond on the glycerol moiety. In one embodiment, the monoglyceride is a 1-monoacylglycerol. Representative 1-monoacylglycerols and 2-monoacylglycerols are shown below having the general formula IIA and IIB respectively, wherein $R_7$ is as defined above.

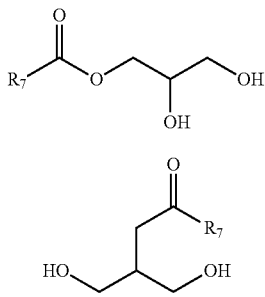

IIA

IIB

In a particular embodiment, the monoglyceride has formula IIC.

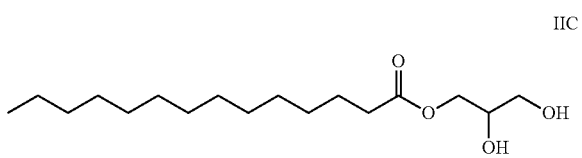 [SMILES: CCCCCCCCCCCCCC(=O)OCC(O)CO]

IIC

Free fatty acids for use in the present disclosure have the general formula III.

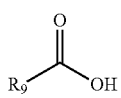

III wherein $R_9$ is a saturated or unsaturated carbon chain.

In one embodiment, the $R_9$ group is a saturated carbon chain. In another embodiment, the $R_9$ group is an unsaturated carbon chain; when $R_9$ is an unsaturated carbon chain, the carbon chain may contain from 1 to 6, from 1 to 4 or from 1 to 3 double bonds. In another embodiment, the $R_9$ group is a carbon chain up to 5 carbons in length, a carbon chain from 6 to 12 carbons in length, a carbon chain from 13-21 carbons in length and a carbon chain greater than 22 carbons in length; in a particular embodiment, the carbon chain is from 13 to 21 carbons in length. Such carbon chain, regardless of the length, includes both even and odd chain lengths. In another embodiment, the $R_9$ group has a carbon chain length of 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55 or more carbons, which are saturated or unsaturated. In another embodiment, the $R_9$ group has a carbon chain length of 3, 4, 5, 6, 7, 8, 9, 10, 11, 12, 13, 14, 15, 16, 17, 18, 19, 20 or 21 carbons, which are saturated or unsaturated. In another embodiment, the $R_9$ group has a carbon chain length of 10, 11, 12, 13, 14, 15, 16, 17, 18, 19, 20 or 21 carbons, which are saturated or unsaturated. In another embodiment, the $R_9$ group has a carbon chain length of 12, 13, 14, 15 or 16, carbons, which are saturated or unsaturated. In another embodiment, the $R_9$ group has a carbon chain length of 14 carbons, which is saturated.

In a particular embodiment, the fatty acid has formula IIIA.

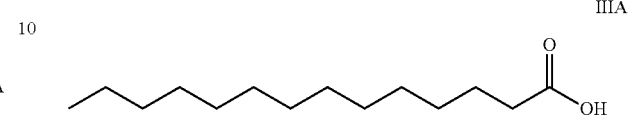

IIIA

In a particular embodiment, the composition comprises a lysophosphatidyl compound of the formula I and at least one of a monoglyceride of the general formula II, a free fatty acid of the general formula III, or a combination of a monoglyceride of the general formula II and a free fatty acid of the general formula III. In one aspect of this embodiment, $R_1$ of the lysophosphatidyl compound of the formula I, $R_7$ of the monoglyceride of the general formula II and $R_9$ of the free fatty acid of the general formula III each have the same chain length.

In another particular embodiment, the composition comprises a lysophosphatidyl compound of the formula IA and at least one of a monoglyceride of the general formula II, a free fatty acid of the general formula III, or a combination of a monoglyceride of the general formula II and a free fatty acid of the general formula III. In one aspect of this embodiment, $R_1$ of the lysophosphatidyl compound of the formula IA, $R_7$ of the monoglyceride of the general formula II and $R_9$ of the free fatty acid of the general formula III each have the same chain length.

In another particular embodiment, the composition comprises a lysophosphatidyl compound of the formula IB and at least one of a monoglyceride of the general formula II, a free fatty acid of the general formula III, or a combination of a monoglyceride of the general formula II and a free fatty acid of the general formula III. In one aspect of this embodiment, $R_1$ of the lysophosphatidyl compound of the formula IB, $R_7$ of the monoglyceride of the general formula II and $R_9$ of the free fatty acid of the general formula III each have the same chain length.

In another particular embodiment, the composition comprises a lysophosphatidyl compound of the formula IC, ID or IE and at least one of a monoglyceride of the general formula II, a free fatty acid of the general formula III, or a combination of a monoglyceride of the general formula II and a free fatty acid of the general formula III. In one aspect of this embodiment, $R_1$ of the lysophosphatidyl compound of the formula IC, ID and IE, $R_7$ of the monoglyceride of the general formula II and $R_9$ of the free fatty acid of the general formula III each have the same chain length.

In another particular embodiment, the composition comprises a lysophosphatidyl compound of the formula IF, IG or IH and at least one of a monoglyceride of the general formula II, a free fatty acid of the general formula III, or a combination of a monoglyceride of the general formula II and a free fatty acid of the general formula III. In one aspect of this embodiment, $R_1$ of the lysophosphatidyl compound of the formula IF, IF and IH, $R_7$ of the monoglyceride of the general formula II and $R_9$ of the free fatty acid of the general formula III each have the same chain length.

In another particular embodiment, the composition comprises a lysophosphatidyl compound of the formula IJ and at least one of a monoglyceride of the general formula II, a free fatty acid of the general formula III, or a combination of a monoglyceride of the general formula II and a free fatty acid of the general formula III. In one aspect of this embodiment, $R_7$ of the monoglyceride of the general formula II and $R_9$ of the free fatty acid of the general formula III are each saturated carbon chains of 13 carbons in length.

In another particular embodiment, the composition comprises a lysophosphatidyl compound of the formula IK and at least one of a monoglyceride of the general formula II, a free fatty acid of the general formula III, or a combination of a monoglyceride of the general formula II and a free fatty acid of the general formula III. In one aspect of this embodiment, $R_7$ of the monoglyceride of the general formula II and $R_9$ of the free fatty acid of the general formula III are each saturated carbon chains of 13 carbons in length.

In any of the foregoing, the monoglyceride may have the structure of the general formula IIA or IIB. In any of the foregoing, the monoglyceride may have the structure of the general formula IIC.

In any of the foregoing, the free fatty acid may have the structure of the general formula IIIA.

In still another particular embodiment, the composition comprises a lysophosphatidyl compound of the formula IJ, at least one of a monoglyceride of the general formula IIC, a free fatty acid of the general formula IIIA, or a combination of a monoglyceride of the general formula IIC and a free fatty acid of the general formula IIIA.

In still another particular embodiment, the composition comprises a lysophosphatidyl compound of the formula IK and at least one a monoglyceride of the general formula IIC, a free fatty acid of the general formula MA, or a combination of a monoglyceride of the general formula IIC and a free fatty acid of the general formula MA.

In a further particular embodiment, the composition comprises a lysophosphatidyl compound of the formula IJ, a monoglyceride of the general formula IIC and a free fatty acid of the general formula IIIA.

In a further particular embodiment, the composition comprises a lysophosphatidyl compound of the formula IK, a monoglyceride of the general formula IIC and a free fatty acid of the general formula IIIA.

In one embodiment, the composition of the present disclosure is adapted for oral administration. In a particular embodiment, the composition of the present disclosure forms a eutectic mixture.

In certain embodiments, the compositions have the following abbreviations, chemical names and structures:

Curcumin (368.38) (MW)

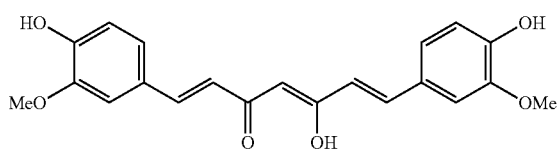 [SMILES: COc1cc(/C=C/C(=O)/C=C(O)/C=C/c2ccc(O)c(OC)c2)ccc1O]

DMPC: 1,2-dimyristoyl-sn-glycero-3-phosphocholine (677.94) (MW)

General Term—Phosphatidyl Choline

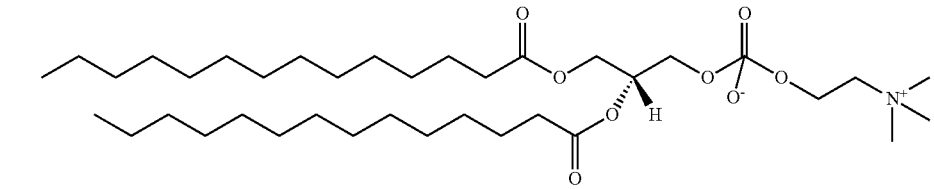

DMPG: 1,2-dimyristoyl-sn-glycero-3-[phosphoric-(1-glycerol)] (sodium salt) (688.86) (MW)

General Term—Phosphatidyl Glycerol

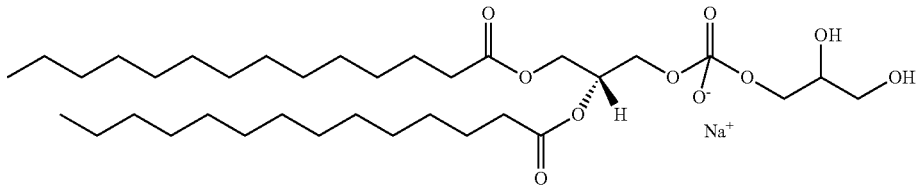

14:0 LysoPG, 14:0 LPG, 14:0 lysophosphatidylglycerol, myristoyl lysophosphatidylglycerol: 1-myristoyl-2-hydroxy-sn-glycero-3-[phospho-rac-(1-glycerol)] sodium salt (478) (MW)

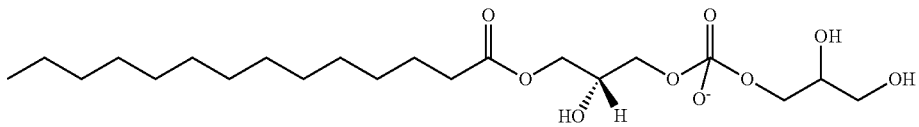

| 19 | 20 |
|---|---|
| 14:0 Monoglyceride Myristoyl Monoglyceride (302) (MW) | Myristic Acid, Free Fatty Acid (228) (MW) |
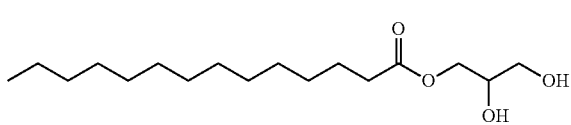 [SMILES: CCCCCCCCCCCCCC(=O)OCC(O)CO]
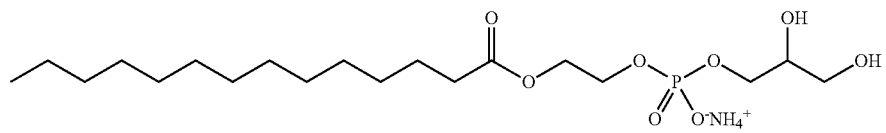
14:0 EGPG, ethylene glycol PG: 2,3-dihydroxypropyl(2-[tetradecanoyloxy]ethyl)phosphate (ammonium salt) (444) (MW)
Lysophosphatidic Acid—e.g., 18:1 LPA
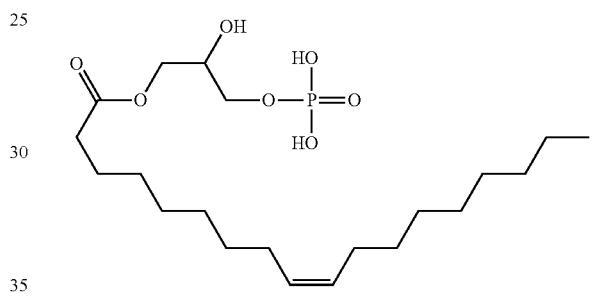
Arachidonic Acid 20:4 (304.5)
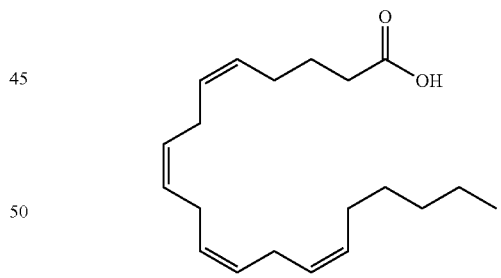
Cardiolipin
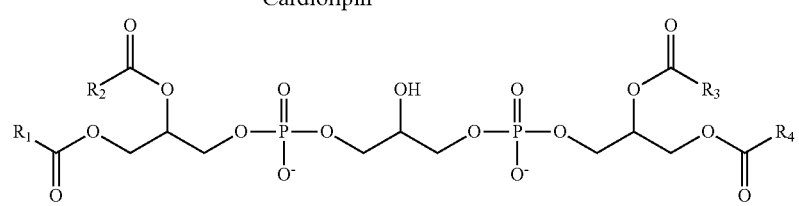

10:0 LysoPG: 1-decanoyl-2-hydroxy-sn-glycero-3-[phospho-rac-(1-glycerol)] sodium salt 12:0 LysoPG: 1-dodecanoyl-2-hydroxy-sn-glycero-3-[phospho-rac-(1-glycerol)] sodium salt 16:0 LysoPG: 1-palmitoyl-2-hydroxy-sn-glycero-3-[phospho-rac-(1-glycerol)] sodium salt 18:0 LysoPG: 1-stearoyl-2-hydroxy-sn-glycero-3-[phospho-rac-(1-glycerol)] sodium salt Generic name for acyl-LPGs=1-acyl-2-hydroxy-sn-glycero-3-phospho-glycerol (LPG)

As used herein, the term "eutectic blend" refers to a mixture of chemical compounds or elements that have a chemical composition that solidifies at a lower temperature than other composition made up of the same ingredients. For example, one blended eutectic (referred to herein as EU8120) is composed of three components (14:0 Lysophosphatidylglycerol (Lyso PG), Myristoyl monoglyceride, and Myristic acid, a free fatty acid). In one non-limiting example, the blended eutectic can be made to enhance the oral bioavailability of LysoPG.

14:0 Lysophosphatidylglycerol (Lyso PG)

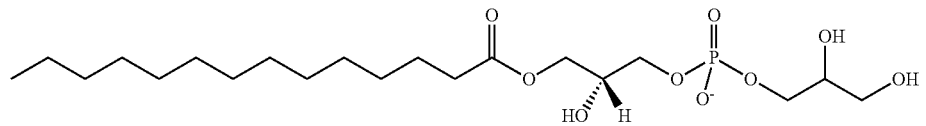 [SMILES: CCCCCCCCCCCCCC(=O)OC[C@@H](O)COP(=O)([O-])OCC(O)CO]

Myristoyl Monoglyceride

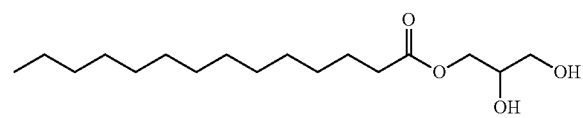 [SMILES: CCCCCCCCCCCCCC(=O)OCC(O)CO]

Myristic Acid, a Free Fatty Acid

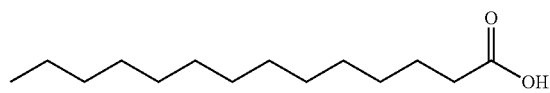 [SMILES: CCCCCCCCCCCCCC(=O)O]

As discussed above, the free (non-esterified) fatty acids and the esterified fatty acids of the monoglyceride component may be saturated or unsaturated. If the free fatty acids of the composition are saturated, sufficient quantities of mono-valent and divalent cations may be optionally added to form fatty acid salts. In one embodiment, the cations are present at a molar concentration of approximately one-half of the molar amount of the fatty acid. Suitable cations include sodium and calcium ions. Furthermore the lysophosphatidyl compounds and monoglyceride compounds of the present disclosure may be present as salts as well.

In one embodiment, the free fatty acid and monoglyceride are present in the composition in a molar ratio of between about 2:1 and 1:2 (including any subrange therebetween, such as 1:1). In one embodiment, the free fatty acid and monoglyceride comprise from about 70 mole to 99 mole percent of the composition, with the lysophosphatidyl compound comprising from about 30 mole percent to 1 mole percent of the composition. The above mole percentages are expressed with regard to the lipid components of the composition. In one embodiment, the lysophosphatidyl compound to free fatty acid and monoglyceride are present in the composition in a molar ratio of between about 1:6 and 1:3 (including any subrange therebetween, such as 1:1). In one embodiment, the lysophosphatidyl compound to free fatty acid and monoglyceride are present in the composition in a molar ratio of greater than or equal to 1:6. In one embodiment, the lysophosphatidyl compound to free fatty acid and monoglyceride are present in the composition in a molar ratio of greater than or equal to 1:3. In one embodiment, the lysophosphatidyl compound to free fatty acid and monoglyceride are present in the composition in a molar ratio of greater than or equal to 1:2. In a particular aspect, the foregoing applies to compositions of the present disclosure.

In one embodiment, the ratios of the components of the composition are between about 1:4:2 to 1:2:4 (including any subrange therebetween) mole percent lysophosphatidyl compound:monoglyceride:free fatty acid. In another embodiment, the ratios of the components of the composition are 1:4:2 mole percent lysophosphatidyl compound:monoglyceride:free fatty acid. In another embodiment, the ratios of the components of the composition are 1:3:3 mole percent lysophosphatidyl compound:monoglyceride:free fatty acid. In still another embodiment, the ratios of the components of the composition are 1:2:4 mole percent lysophosphatidyl compound:monoglyceride:free fatty acid. In another embodiment, the ratios of the components of the composition are 1:2:1 mole percent lysophosphatidyl compound:monoglyceride:free fatty acid. In another embodiment, the ratios of the components of the composition are 2:4:2 mole percent lysophosphatidyl compound:monoglyceride:free fatty acid. In a particular aspect, the foregoing applies to compositions of the present disclosure.

In one embodiment, the PL to drug ratio are between about 15:1 and 0.03:1 (including any subrange therebetween, such as 3:1). In another embodiment, the PL to drug ratio are between about 9:1 and 0.1:1. In another embodiment, the PL to drug ratio are between about 3:1 and 0.3:1. In another embodiment, the PL to drug ration is about 9:1. In another embodiment, the PL to drug ration is about 3:1. In another embodiment, the PL to drug ration is about 1:1. In another embodiment, the PL to drug ration is about 0.3:1. In another embodiment, the PL to drug ration is about 0.1:1. In a particular aspect, the foregoing applies to a composition where the ratios of the components of the composition are between about 1:4:2 to 1:2:4 (including any subrange therebetween, such as 1:4:2, 1:2:1, 2:4:2, 1:3:3 and 1:2:4) mole percent lysophosphatidyl compound:monoglyceride:free fatty acid.

The present invention can be used with any QT prolonging drug, including but not limited to those listed at: www.crediblemeds.org, Albuterol (salbutamol), Alfuzosin, Amantadine, Amiodarone, Amisulpride, Amitriptyline, Amoxapine, Amphetamine, Anagrelide, Apomorphine, Arformoterol, Aripiprazole, Arsenic trioxide, Astemizole, Atazanavir, Atomoxetine, Azithromycin, Bedaquiline, Bepridil, Bortezomib, Bosutinib, Chloral hydrate, Chloroquine, Chlorpromazine, Ciprofloxacin, Cisapride, Citalopram, Clarithromycin, Clomipramine, Clozapine, Cocaine, Crizotinib, Dabrafenib, Dasatinib, Desipramine, Dexmedetomidine, Dexmethylphenidate, Dextroamphetamine (d-Amphetamine), Dihydroartemisinin and piperaquine, Diphenhydramine, Disopyramide, Dobutamine, Dofetilide, Dolasetron, Domperidone, Dopamine, Doxepin, Dronedarone, Droperidol, Ephedrine, Epinephrine (Adrenaline), Eribulin, Erythromycin, Escitalopram, Famotidine, Felbamate, Fenfluramine, Fingolimod, Flecainide, Fluconazole, Fluoxetine, Formoterol, Foscarnet, Fosphenytoin, Furosemide (Frusemide), Galantamine, Gatifloxacin, Gemifloxacin, Granisetron, Halofantrine, Haloperidol, Hydrochlorothiazide, Ibutilide, Iloperidone, Imipramine (melipramine), Indapamide, Isoproterenol, Isradipine, Itraconazole, Ivabradine, Ketoconazole, Lapatinib, Levalbuterol (levsalbutamol), Levofloxacin, Levomethadyl, Lisdexamfetamine, Lithium, Mesoridazine, Metaproterenol, Methadone, Methamphetamine (methamfetamine), Methylphenidate, Midodrine, Mifepristone, Mirabegron, Mirtazapine, Moexipril/HCTZ, Moxifloxacin, Nelfinavir, Nicardipine, Nilotinib, Norepinephrine (noradrenaline), Norfloxacin, Nortriptyline, Ofloxacin, Olanzapine, Ondansetron, Oxytocin, Paliperidone, Paroxetine, Pasireotide, Pazopanib, Pentamidine, Perflutren lipid microspheres, Phentermine, Phenylephrine, Phenylpropanolamine, Pimozide, Posaconazole, Probucol, Procainamide, Promethazine, Protriptyline, Pseudoephedrine, Quetiapine, Quinidine, Quinine sulfate, Ranolazine, Rilpivirine, Risperidone, Ritodrine, Ritonavir, Roxithromycin, Salmeterol, Saquinavir, Sertindole, Sertraline, Sevoflurane, Sibutramine, Solifenacin, Sorafenib, Sotalol, Sparfloxacin, Sulpiride, Sunitinib, Tacrolimus, Tamoxifen, Telaprevir, Telavancin, Telithromycin, Terbutaline, Terfenadine, Tetrabenazine, Thioridazine, Tizanidine, Tolterodine, Toremifene, Trazodone, Trimethoprim-Sulfa, Trimipramine, Vandetanib, Vardenafil, Vemurafenib, Venlafaxine, Voriconazole, Vorinostat, or Ziprasidone.

The active agent can also be selected from at least one of an adrenergic agent; adrenocortical steroid; adrenocortical suppressant; aldosterone antagonist; analgesic; anesthetic; anti-acne agent; anti-adrenergic; anti-allergic; anti-amebic; anti-anemic; anti-anginal; anti-arthritic; anti-asthmatic; anti-atherosclerotic; antibacterial; anticholinergic; anticoagulant; anticonvulsant; antidepressant; antidiabetic; antidiarrheal; antidiuretic; anti-emetic; anti-epileptic; antifibrinolytic; antifungal; antihemorrhagic; antihistamine; antihyperlipidemia; antihypertensive; antihypotensive; anti-infective; anti-inflammatory; antimicrobial; antimigraine; antimitotic; antimycotic, antinauseant, antineoplastic, antineutropenic, antiparasitic; antiproliferative; antipsychotic; antirheumatic; antiseborrheic; antisecretory; antispasmodic; antithrombotic; anti-ulcerative; antiviral; appetite suppressant; blood glucose regulator; bone resorption inhibitor; bronchodilator; cardiovascular agent; cholinergic; depressant; diagnostic aid; diuretic; dopaminergic agent; estrogen receptor agonist; fibrinolytic; gastric acid supressant; gastrointestinal motility effector; glucocorticoid; hemostatic; histamine H2 receptor antagonists; hypocholesterolemic; hypoglycemic; hypolipidemic; hypotensive; immunomodulator; immunostimulant; immunosuppressant; LHRH agonist; mood regulator; nasal decongestant; neuromuscular blocking agent; neuroprotective; NMDA antagonist; non-hormonal sterol derivative; psychotropic; sedative; sedative-hypnotic; selective adenosine A1 antagonist; serotonin antagonist; serotonin inhibitor; serotonin receptor antagonist; steroid; tranquilizer; unstable angina agent; vasoconstrictor; or vasodilator.

Human ether-a-go-go-related gene (hERG) Potassium channel anti-blockade by liposome and fragments.

Potassium channels conduct the rapid component of the delayed rectifier potassium current, $I_{Kr}$, which is crucial for repolarization of cardiac action potentials. A reduction in hERG currents due to either genetic defects or adverse drug effects can lead to hereditary or acquired long QT syndromes characterized by action potential prolongation, lengthening of the QT interval on the surface ECG, and an increased risk for torsade de pointes arrhythmias and sudden death. This undesirable side effect of non-antiarrhythmic compounds has prompted the withdrawal of drugs from the market. Studies on mechanisms of hERG channel inhibition provide significant insights into the molecular factors that determine state-, voltage-, and use-dependency of hERG current block. Mutations altering properties of the high-affinity drug binding site in hERG and its interaction with drug molecules cause current increase and hereditary short QT syndrome with a high risk for life-threatening arrhythmias. (Thomas D1, 2006).

Anatomical Characteristics of the K+ Channel.

The types and distributions of inwardly rectifying potassium ($I_{Kr}$) channels are one of the major determinants of the electrophysiological properties of cardiac myocytes. Inward rectifier potassium ($I_{Kr}$) channels regulate cell excitability and transport of K+ ions across cell membranes.

The potassium channel from *Streptomyces lividans* is an integral membrane protein with sequence similarity to all known K+ channels, particularly in the pore region. X-ray analysis with data to 3.2 angstroms reveals that four identical subunits create an inverted teepee, or cone, cradling the selectivity filter of the pore in its outer end. The narrow selectivity filter is only 12 angstroms long, whereas the remainder of the pore is wider and lined with hydrophobic amino acids. A large water-filled cavity and helix dipoles are positioned so as to overcome electrostatic destabilization of an ion in the pore at the center of the bilayer. Main chain carbonyl oxygen atoms from the K+ channel signature sequence line the selectivity filter, which is held open by structural constraints to coordinate K+ ions but not smaller Na+ ions. The selectivity filter contains two K+ ions about 7.5 angstroms apart. Ion channels exhibit ion selectivity through pore architecture that conducts specific ions. This configuration promotes ion conduction by exploiting electrostatic repulsive forces to overcome attractive forces between K+ ions and the selectivity filter. The architecture of the pore establishes the physical principles underlying selective K+ conduction (Doyle D A, 1998).

Another member of the inward-rectifier family of potassium channels is the prokaryotic KirBac1.1 channel. The structure of the $I_{Kr}$ channel assembly in the closed state, when refined to a resolution of 3.65 angstroms, contains a main activation gate and structural elements involved in gating. On the basis of structural evidence, gating involves coupling between the intracellular and membrane domains suggesting that initiation of gating by membrane or intracellular signals represents different entry points to a common mechanistic pathway. (Kuo, A 2003).

$I_{Kr}$ channels in the cardiac myocytes may be actively regulated by means of the change in PIP(2) level rather than by downstream signal transduction pathways. The classical inward rectifier K(+) channel), Kir2.1, Kir6.2/SUR2A (ATP-sensitive K(+) channel) and Kir3.1/3.4 (muscarinic K(+) channels) in cardiac myocytes are commonly upregulated by a membrane lipid, phosphatidylinositol 4,5-bisphosphates (PIP(2)). PIP(2) interaction sites appear to be conserved by positively charged amino acid residues and the putative alpha-helix in the C-terminals of $I_{Kr}$ channels. PIP(2) level in the plasma membrane is regulated by tagonist stimulation (Takano M I 2003).

Inward rectifier potassium channels are characterized by two transmembrane helices per subunit, plus an intracellular C-terminal domain that controls channel gating in response to changes in concentration of various ligands. Based on the crystal structure of the tetrameric C-terminal domain of Kir3.1, it is possible to build a homology model of the ATP-binding C-terminal domain of Kir6.2. Molecular dynamics simulations are used to probe the dynamics of $I_{Kr}$ C-terminal domains and to explore the relationship between their dynamics and possible mechanisms of channel gating. Multiple simulations, each of 10 ns duration, were performed for Kir3.1 (crystal structure) and Kir6.2 (homology model), in both their monomeric and tetrameric forms. The Kir6.2 simulations were performed with and without bound ATP. The results of the simulations reveal comparable conformational stability for the crystal structure and the homology model. There is a decrease in conformational flexibility when comparing the monomers with the tetramers, corresponding mainly to the subunit interfaces in the tetramer. The beta-phosphate of ATP interacts with the side chain of K185 in the Kir6.2 model and simulations. The flexibility of the Kir6.2 tetramer is not changed greatly by the presence of bound ATP, other than in two loop regions. Principal components analysis of the simulated dynamics suggests loss of symmetry in both the Kir3.1 and Kir6.2 tetramers, consistent with "dimer-of-dimers" motion of subunits in C-terminal domains of the corresponding $I_{Kr}$ channels. This is suggestive of a gating model in which a transition between exact tetrameric symmetry and dimer-of-dimers symmetry is associated with a change in transmembrane helix packing coupled to gating of the channel. Dimer-of-dimers motion of the C-terminal domain tetramer is also supported by coarse-grained (anisotropic network model) calculations. Loss of exact rotational symmetry is suggested to play a role in gating in the bacterial $I_{Kr}$ homolog, KirBac1.1, and in the nicotinic acetylcholine receptor channel (Haider S I, 2005).

Homotetrameric models of three mammalian $I_{Kr}$ channels (Kir1.1, Kir3.1, and Kir6.2) have been generated, using the KirBac3.1 transmembrane and rat Kir3.1 intracellular domain structures as templates. All three models were explored by 10 ns molecular dynamics simulations in phospholipid bilayers. Analysis of the initial structures revealed conservation of potential lipid interaction residues (Trp/Tyr and Arg/Lys side chains near the lipid headgroup-water interfaces). Examination of the intracellular domains revealed key structural differences between Kir1.1 and Kir6.2 which may explain the difference in channel inhibition by ATP. The behavior of all three models in the MD simulations revealed that they have conformational stability similar to that seen for comparable simulations of, for example, structures derived from cryoelectron microscopy data. Local distortions of the selectivity filter were seen during the simulations, as observed in previous simulations of KirBac and in simulations and structures of KcsA. These may be related to filter gating of the channel. The intracellular hydrophobic gate does not undergo any substantial changes during the simulations and thus remains functionally closed. Analysis of lipid-protein interactions of the $I_{Kr}$ models emphasizes the key role of the M0 (or "slide") helix which lies approximately parallel to the bilayer-water interface and forms a link between the transmembrane and intracellular domains of the channel (Haider S I, 2007).

The potassium-selective transmembrane pore in voltage-activated K+ channels is gated by changes in the membrane potential. Activation gating (opening) occurs in milliseconds and involves a gate at the cytoplasmic side of the pore. Substituting cysteine at a particular position in the last transmembrane region (S6) of the homotetrameric Shaker K+ channel creates metal binding sites at which Cd2+ ions can bind with high affinity. The bound Cd2+ ions form a bridge between the introduced cysteine in one channel subunit and a native histidine in another subunit, and the bridge traps the gate in the open state. These results suggest that gating involves a rearrangement of the intersubunit contacts at the intracellular end of S6. The structure of a bacterial K+ channel shows that the S6 homologs cross in a bundle, leaving an aperture at the bundle crossing. In the context of this structure, the metal ions form a bridge between a cysteine above the bundle crossing and a histidine below the bundle crossing in a neighboring subunit, which results suggest that gating occurs at the bundle crossing, possibly through a change in the conformation of the bundle itself (Holmgren M L 2002).

Activated gating in voltage-activated K+ channels are a potassium-selective transmembrane pore gated by changes in the membrane potential. This activation gating (opening) occurs in milliseconds and involves a gate at the cytoplasmic side of the pore. Substituting cysteine at a particular position in the last transmembrane region (S6) of the homotetrameric Shaker K+ channel creates metal binding sites at which Cd2+ ions can bind with high affinity. The bound Cd2+ ions form a bridge between the introduced cysteine in one channel subunit and a native histidine in another subunit, and the bridge traps the gate in the open state. These results suggest that gating involves a rearrangement of the intersubunit contacts at the intracellular end of S6. The structure of a bacterial K+ channel shows that the S6 homologs cross in a bundle, leaving an aperture at the bundle crossing. In the context of this structure, the metal ions form a bridge between a cysteine above the bundle crossing and a histidine below the bundle crossing in a neighboring subunit. The results suggest that gating occurs at the bundle crossing, possibly through a change in the conformation of the bundle itself (Holmgren M L 2002).

Channelopathies

The human ether-à-go-go gene related cardiac tetrameric potassium channel, when mutated, can render patients sensitive to over 163 drugs, which may inhibit ion conduction and deregulate action potentials. (Credible Meds) Prolongation of the action potential follows effects in the potassium channel. Ion channel active drugs may directly increase the QTc interval, and increase the risk of torsades de pointes and sudden cardiac death. (Table 1) Exacerbation of cardiomyocyte potassium channel sensitivity to drugs may also be associated with metabolic diseased states including diabetes (Veglio M, 2002) or may be of idiopathic origin.

For these reasons, evaluation of drug effects on cardiomyocyte potassium channel function is a critical step during drug development, and when serious, may be an obstacle to regulatory approval. In whole-cell patch-clamp studies, curcumin inhibited hERG K+ currents in HEK293 cells stably expressing hERG channels in a dose-dependent manner, with $IC_{50}$ value of 5.55 µM. The deactivation, inactivation and the recovery time from inactivation of hERG channels were significantly changed by acute treatment of 10 µM curcumin. Incubation of 20 µM curcumin for 24 h reduced the HEK293 cell viability. Intravenous injection of 20 mg of curcumin in rabbits did not affect the cardiac repolarization manifested by QTc values. (Hu C W 2012). However, is demonstrated herein that specific molecules which antagonize QTc prolonging drugs (Helson L, 2002 Ranjan A, 2014, Shopp G, 2014). These molecules are specific liposomes, or components of liposomes which were initially bound to lipophilic drugs to permit intravenous solubility at physiological conditions, and reduce adverse events. The loci of action appears to be in intra-channel ion selectivity or gating site(s) controlling potassium ion movement: a key functional component of regulation of action potentials which lead downstream to myocyte contraction.

The mechanism of human ether-à-go-go related gene channels blockade may be analogous to the effects of externally applied quaternary ammonium derivatives which indirectly may suggest the mechanism of action of the anti-blockading effect of the DMPC/DMPG liposome or its metabolites. The inhibitory constants and the relative binding energies for channel inhibition indicate that more hydrophobic quaternary ammoniums have higher affinity blockade while cation-π interactions or size effects are not a deterministic factor in channel inhibition by quaternary ammoniums. Also hydrophobic quaternary ammoniums either with a longer tail group or with a bigger head group than tetraethylammonium permeate the cell membrane to easily access the high-affinity internal binding site in the gene channel and exert a stronger blockade.

By way of explanation, and in no way a limitation of the present invention, these data show that the basis for the ameliorating effect liposome, or its components is the higher competitive affinity for binding sites by the, DMPC and DMPG compared to QTc prolonging drugs, its constitutive lack of ion transport modulation, i.e., liposome or its fragments do not impede K+ ion transport.

By way of explanation, and in no way a limitation of these claims, these data suggest that the basis for the ameliorating effect liposome, or its components, is the higher competitive affinity for binding sites by the DMPC and DMPG compared to QTc prolonging drugs, its constitutive lack of ion transport modulation, i.e., liposome, or its fragments, do not impede K+ ion transport and indicates that the site of the mechanism of DMPC or DMPG protection may be in the selectivity segment of the channel or in the hydration surrounding the ion.

Additionally, based upon these hERG channel data, the structures of these liposome components may be informative for designing or selecting other molecules to prevent drug induced cardiac arrhythmias.

This study provides additional information as to the QTc modulating effects by drugs, induced in cardiac myocyte potassium channels, and mitigation by liposomes and liposomal constituents. The latter molecules present an opportunity to probe the K$^+$ channels as targets for pharmacological mitigation of drug-induced channelopathies.

Evaluation of the protective effect of DMPC, DMPG, DMPC/DMPG, LysoPG and LysoPC against hERG inhibition by Nilotinib.

Purpose of the study: The purpose of this study is to evaluate in vitro the protective effect of DMPC, DMPG, DMPC/DMPG, LysoPG and LysoPC on the rapidly activating delayed-rectifier potassium selective current ($I_{Kr}$) generated under normoxic conditions in stably transfected Human Embryonic Kidney cells (HEK 293 cells). This study was designed as a screen and does not require QA involvement (non-GLP-compliant).

Test Samples:
1—DMPC
2—DMPG
3—DMPC/DMPG 90:9
4—14:0 LysoPC
5—14:0 LysoPG
6—DMPC+Nilotinib (0.1 µM)
7—DMPG+Nilotinib (0.1 µM)
8—DMPC/DMPG 90:9+Nilotinib (0.1 µM)
9—14:0 LysoPC+Nilotinib (0.1 µM)
10—14:0 LysoPG+Nilotinib (0.1 µM)

Test System: hERG-expressing HEK 293 transfected cell line. Test performed: Whole-cell patch-clamp current acquisition and analysis. Experimental Temperature: 35±2° C.

Application of test samples: 5 minutes of exposure to each concentration in presence of closed circuit perfusion (2 mL/min). 5 minutes for washout periods in presence of a flow-through perfusion (2 mL/min) in addition to a closed circuit perfusion (2 mL/min). The positive control (Nilotinib, 0.05 µg/mL) was added to naive cells obtained from the same cell line and same passage for a period of 5 minutes in presence of a closed circuit perfusion (2 mL/min).

Cells were under continuous stimulation of the pulses protocol throughout the studies and cell currents were recorded after 5 minutes of exposure to each condition.

Original data acquisition design: Acquisition Rate(s): 1.0 kHz.

Design for acquisition when testing the compound or the vehicle/solvent equivalent:
1 recording made in baseline condition
1 recording made in the presence of concentration 1
Design for acquisition when testing the positive control:
1 recording made in baseline condition
1 recording made in the presence of the positive control
n=number of responsive cells patched on which the whole protocol above could be applied.

Statistical analysis: Statistical comparisons were made using paired Student's t-tests. The currents recorded obtained on day 2, 3 and 4 were statistically compared to the currents recorded on day 1.

The currents recorded after the positive control (nilotinib alone) exposure were compared to the currents recorded in baseline conditions.

Differences were considered significant when p≤0.05.

Exclusion Criteria:
1. Timeframe of drug exposure not respected
2. Instability of the seal
3. No tail current generated by the patched cell
4. No significant effect of the positive control
5. More than 10% variability in capacitance transient amplitude over the duration of the Study.

Effect of the Test samples on whole-cell $I_{Kr}$, hERG currents. Whole-cell currents elicited during a voltage pulse were recorded in baseline conditions and following the application of the selected concentration of test sample. The cells were depolarized for one second from the holding potential (−80 mV) to a maximum value of +40 mV, starting at −40 mV and progressing in 10 mV increments. The membrane potential was then repolarized to −55 mV for one second, and finally returned to −80 mV.

Whole-cell tail current amplitude was measured at a holding potential of −55 mV, following activation of the current from −40 to +40 mV. Current amplitude was measured at the maximum (peak) of this tail current. Current density was obtained by dividing current amplitude by cell capacitance measured prior to capacitive transient minimization.

Current run-down and solvent effect correction. All data points presented in this Study Report have been corrected for solvent effect and time-dependent current run-down. Current run-down and solvent effects were measured simultaneously by applying the experimental design in test-article free conditions over the same time frame as was done with the test sample. The loss in current amplitude measured during these so-called vehicle experiments (representing both solvent effects and time-dependent run-down) was subtracted from the loss of amplitude measured in the presence of the test sample to isolate the effect of the test sample, apart from the effect of the solvent and the inevitable run-down in current amplitude over time.

TABLE 1

Effect of DMPC, DMPC + Nilotinib and Nilotinib on hERG current density from transfected HEK 293 cells.

| | Normalized Current Density | Corrected Normalized Current Density | SEM | P value | n = |
|---|---|---|---|---|---|
| Baseline | 1.000 | 1.000 | n/a | n/a | 3 |
| DMPC | 0.863 | 1.056 | 0.056 | 0.423 | 3 |
| Nilotinib, 0.1 µM | 0.308 | 0.459* | 0.070 | 0.016 | 3 |
| DMPC + Nilotinib, 0.1 µM | 0.836 | 1.029 | 0.023 | 0.328 | 3 |

FIG. 1 is a graph that shows the effect of DMPC, DMPC+Nilotinib and Nilotinib on hERG current density from transfected HEK 293 cells.

TABLE 2

Effect of DMPG, DMPG + Nilotinib and Nilotinib on hERG current density from transfected HEK 293 cells.

| | Normalized Current Density | Corrected Normalized Current Density | SEM | p value | n = |
|---|---|---|---|---|---|
| Baseline | 1.000 | 1.000 | n/a | n/a | 3 |
| DMPG | 0.800 | 0.994 | 0.044 | 0.901 | 3 |
| Nilotinib, 0.1 µM | 0.308 | 0.459* | 0.070 | 0.016 | 3 |
| DMPG + Nilotinib, 0.1 µM | 0.743 | 0.936 | 0.067 | 0.437 | 3 |

Figure 2:
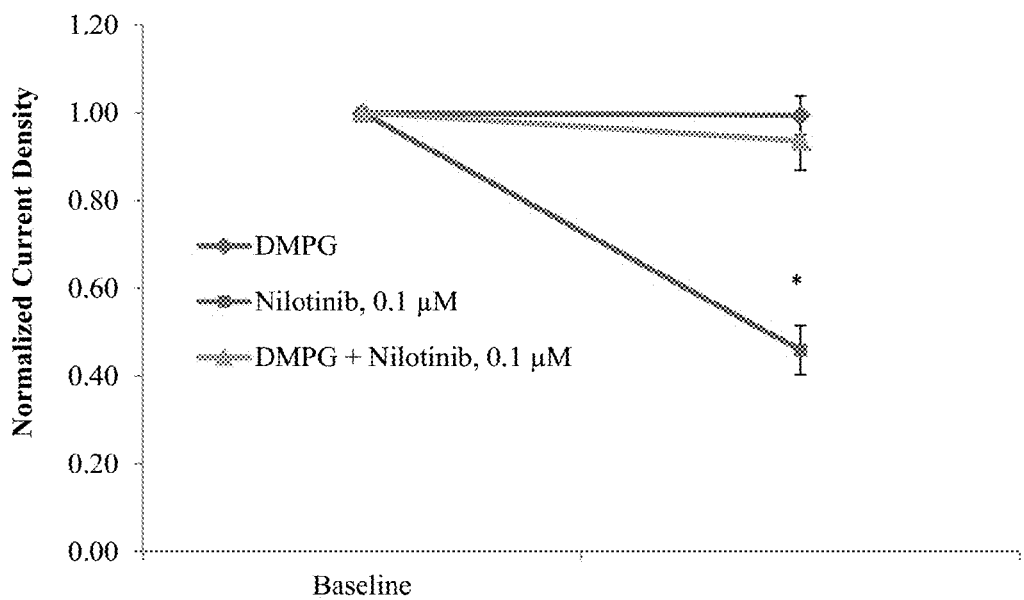
FIG. 2 is a graph that shows the effect of DMPG, DMPG+Nilotinib and Nilotinib on hERG current density from transfected HEK 293 cells.

FIG. 2 is a graph that shows the effect of DMPG, DMPG+Nilotinib and Nilotinib on hERG current density from transfected HEK 293 cells.

TABLE 3

Effect of DMPC/DMPG, DMPC/DMPG + Nilotinib and Nilotinib on hERG current density from transfected HEK 293 cells.

| | Normalized Current Density | Corrected Normalized Current Density | SEM | P value | n = |
|---|---|---|---|---|---|
| Baseline | 1.000 | 1.000 | n/a | n/a | 3 |
| DMPC-DMPG | 0.871 | 1.064 | 0.127 | 0.647 | 4 |
| Nilotinib, 0.1 µM | 0.308 | 0.459* | 0.070 | 0.016 | 3 |
| DMPC/DMPG + Nilotinib, 0.1 µM | 0.773 | 0.966 | 0.098 | 0.754 | 4 |

Figure 3:
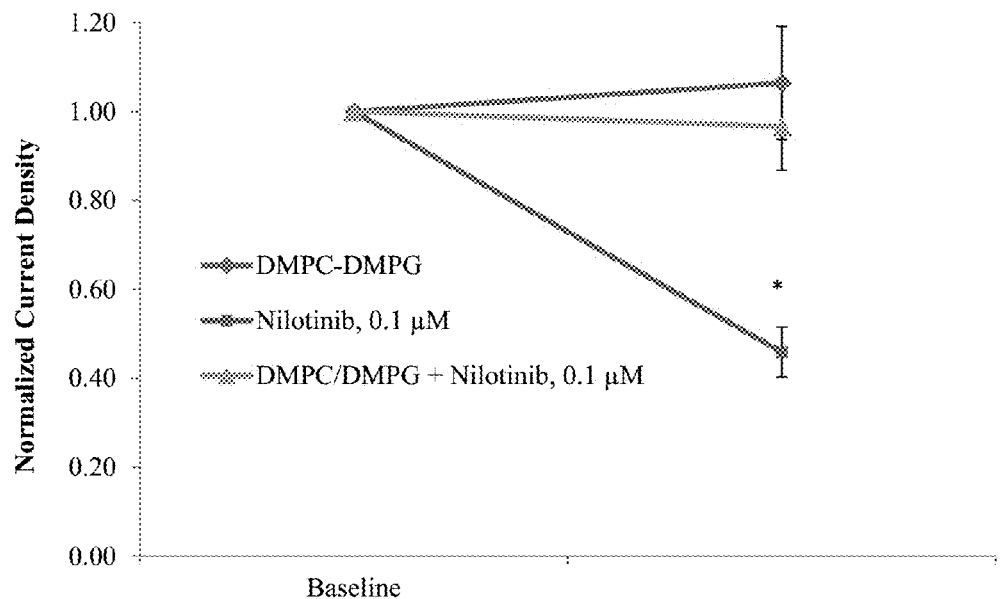
FIG. 3 is a graph that shows the effect of DMPC/DMPG, DMPC/DMPG+Nilotinib and Nilotinib on hERG current density from transfected HEK 293 cells.

FIG. 3 is a graph that shows the effect of DMPC/DMPG, DMPC/DMPG+Nilotinib and Nilotinib on hERG current density from transfected HEK 293 cells.

TABLE 4

Effect of LysoPC, LysoPC + Nilotinib and Nilotinib on hERG current density from transfected HEK 293 cells.

| | Normalized Current Density | Corrected Normalized Current Density | SEM | P value | n = |
|---|---|---|---|---|---|
| Baseline | 1.000 | 1.000 | n/a | n/a | 3 |
| LysoPC | 0.647 | 0.840* | 0.040 | 0.028 | 4 |
| Nilotinib, 0.1 µM | 0.308 | 0.459* | 0.070 | 0.016 | 3 |
| LysoPC + Nilotinib, 0.1 µM | 0.865 | 1.097 | 0.055 | 0.553 | 3 |

Figure 4:
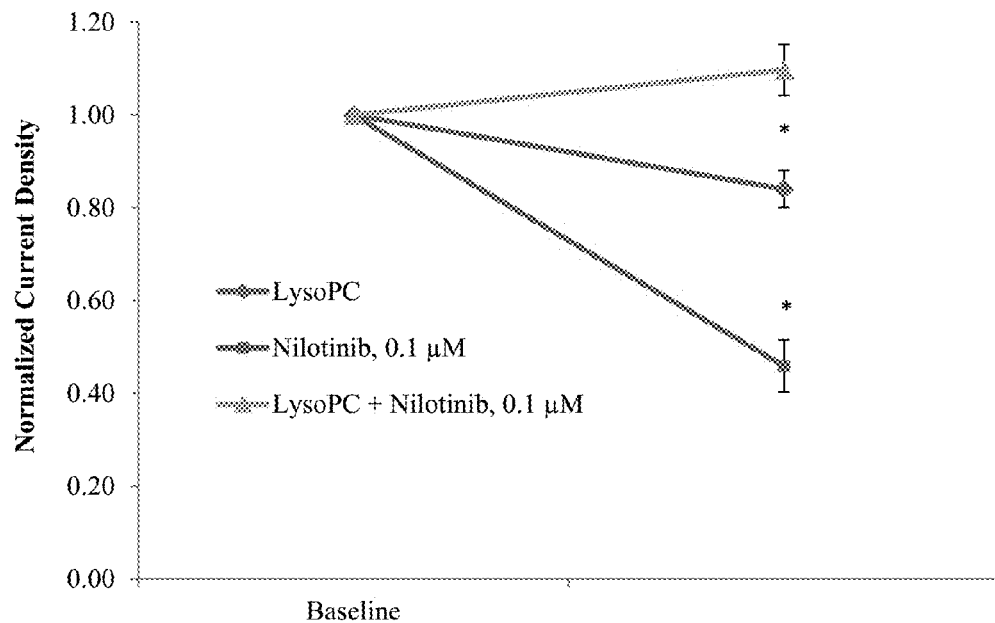
FIG. 4 is a graph that shows the effect of LysoPC, LysoPC+Nilotinib and Nilotinib on hERG current density from transfected HEK 293 cells.

FIG. 4 is a graph that shows the effect of LysoPC, LysoPC+Nilotinib and Nilotinib on hERG current density from transfected HEK 293 cells.

TABLE 5

Effect of LysoPG, LysoPG + Nilotinib and Nilotinib on hERG current density from transfected HEK 293 cells.

| | Normalized Current Density | Corrected Normalized Current Density | SEM | p value | n = |
|---|---|---|---|---|---|
| Baseline | 1.000 | 1.000 | n/a | n/a | 3 |
| 14:0 LysoPG, 0.45 µg/mL | 0.930 | 1.124 | 0.128 | 0.435 | 3 |
| Nilotinib, 0.1 µM | 0.308 | 0.459* | 0.070 | 0.016 | 3 |
| 14:0 LysoPG + Nilotinib, 0.1 µM | 0.743 | 0.936 | 0.067 | 0.437 | 3 |

Figure 5:
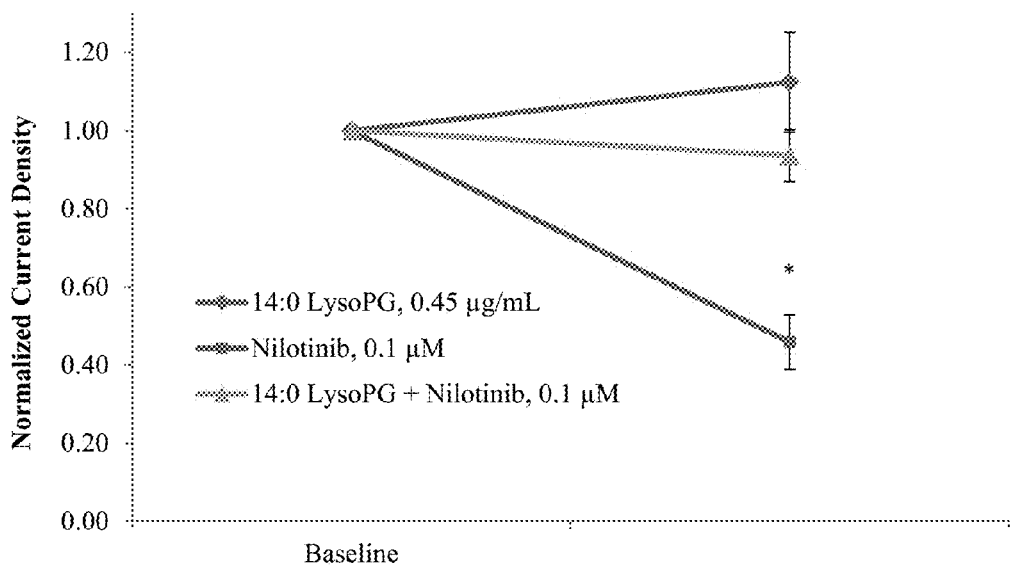
FIG. 5 is a graph that shows the effect of LysoPG, LysoPG+Nilotinib and Nilotinib on hERG current density from transfected HEK 293 cells.

FIG. 5 is a graph that shows the effect of LysoPG, LysoPG+Nilotinib and Nilotinib on hERG current density from transfected HEK 293 cells.

This study aimed at quantifying the protective effect of DMPC, DMPG, DMPC/DMPG, LysoPG and LysoPC against the inhibition of the rapidly activating delayed-rectifier potassium selective current (IKr) generated under normoxic conditions in stably transfected Human Embryonic Kidney (HEK) 293 cells caused by the Nilotinib.

All data points presented in this study have been corrected for solvent effects and time-dependent current run-down. These two parameters were evaluated by applying exactly the same experimental design to the vehicle as that done with the test samples. The currents were measured over the same time course as was done in the presence of the test sample. The values obtained, representing both solvent effects and time-dependent run-down, were used to correct the effect of the test samples, if any. This ensures that changes attributable to time or the solvent are not mistakenly attributed to the test samples.

DMPC, DMPG, DMPC/DMPG and LysoPG alone did not cause any inhibition of the hERG tail current density (n=3). LysoPC alone caused 16% of inhibition of the hERG tail current density (n=4).

Nilotinib alone, formulated in DMSO at 0.1 µM, caused 54.1% of inhibition of the hERG tail current (n=3). The inhibition observed is in line with previous data generated in identical conditions, and agrees with reported inhibition values for this compound.

Nilotinib when formulated in an aqueous solution containing DMPC, DMPG, DMPC/DMPC, LysoPG or LysoPC (ratio 1:9) did not cause any inhibition of the hERG tail current.

These data suggest that co-formulating Nilotinib with DMPC, DMPG, DMPC/DMPC, LysoPG and LysoPC protects against hERG inhibition caused by Nilotinib.

In this study, the DMPC+Nilotinib, DMPG+Nilotinib, DMPC/DMPC+Nilotinib, LysoPG+Nilotinib or LysoPC+Nilotinib were all formulated using the same method. The appropriate amount of Nilotinib powder was dissolved in an aqueous solution containing either DMPC, DMPG, DMPC/DMPG, LysoPG or LysoPC (ratio 9:1). The solution was vortexed for 10 minutes before being used in the patch-clamp assay.

In contrast, the Nilotinib used for the cells exposed to Nilotinib alone was dissolved in DMSO. Additional studies were conducted to determine whether the difference in hERG inhibition between DMSO-formulated Nilotinib and lipid-co-formulated Nilotinib resulted from the different formulations (aqueous or DMSO-based).

Steps for the Study:

| Step 1 | Step 2 | Step 3 | Step 4 |
|---|---|---|---|
| Baseline recording | TA* added into the experimental chamber | 5 minutes exposure time | TA recording |

*TA =
1—DMPC (in aqueous solution)
2—DMPG (in aqueous solution)
3—DMPC/DMPG 90:9 (in aqueous solution)
4—14:0 LysoPC (in aqueous solution)
5—14:0 LysoPG ( in aqueous solution)
6—DMPC + Nilotinib (0.1 μM) (in aqueous solution)
7—DMPG + Nilotinib (0.1 μM) (in aqueous solution)
8—DMPC/DMPG 90:9 + Nilotinib (0.1 μM) (in aqueous solution)
9—14:0 LysoPC + Nilotinib (0.1 μM) (in aqueous solution)
10—14:0 LysoPG + Nilotinib (0.1 μM) (in aqueous solution)
11—Nilotinib alone (in DMSO)

Amongst the mechanisms considered to explain the protection of hERG currents were the possibility that DMPC/DMPG or the Lyso-variants quenched the Nilotinib at the moment of formulation, essentially preventing it from getting into the channel at its receptor site. Another possibility was that Nilotinib was less soluble in an aqueous solution, and therefore was incompletely solubilized at 0.1 μM.

To test both possibilities, Nilotinib was formulated in DMSO and added into the experimental chamber following the addition of the DMPC or DMPG. This was based on the principle that 1—adding DMPC/DMPG alone, followed by DMSO-formulated Nilotinib, would eliminate the possibility of early quenching of Nilotinib by the lysosome; and 2—that DMSO would maintain the solubility of Nilotinib (the "Nilotinib-only" inhibition of hERG was observed when DMSO-formulated Nilotinib was added to the cells).

Steps for the Following Data

| Step 1 | Step 2 | Step 3 | Step 4 | Step 5 | Step 6 |
|---|---|---|---|---|---|
| Baseline recording | DMPC or DMPG added into the experimental chamber | 5 minutes exposure time | DMPC or DMPG recording | Nilotinib in DMSO added into the experimental chamber | DMPC or DMPG + Nilotinib (in DMSO) recording |

TABLE 6

Effect of DMPC, DMPC + Nilotinib, DMPC + Nilotinib (in DMSO) and Nilotinib on hERG current density from transfected HEK 293 cells.

| | Normalized Current Density | Corrected Normalized Current Density | SEM | p value | n = |
|---|---|---|---|---|---|
| Baseline | 1.000 | 1.000 | n/a | n/a | 3 |
| DMPC | 0.863 | 1.056 | 0.056 | 0.423 | 3 |
| Nilotinib, 0.1 μM | 0.308 | 0.459* | 0.070 | 0.016 | 3 |
| DMPC + Nilotinib, 0.1 μM (Aqueous) | 0.836 | 1.029 | 0.023 | 0.328 | 3 |
| DMPC + Nilotinib (in DMSO), 0.1 μM | 0.164 | 0.358* | 0.020 | 0.019 | 2 |

Figure 6:
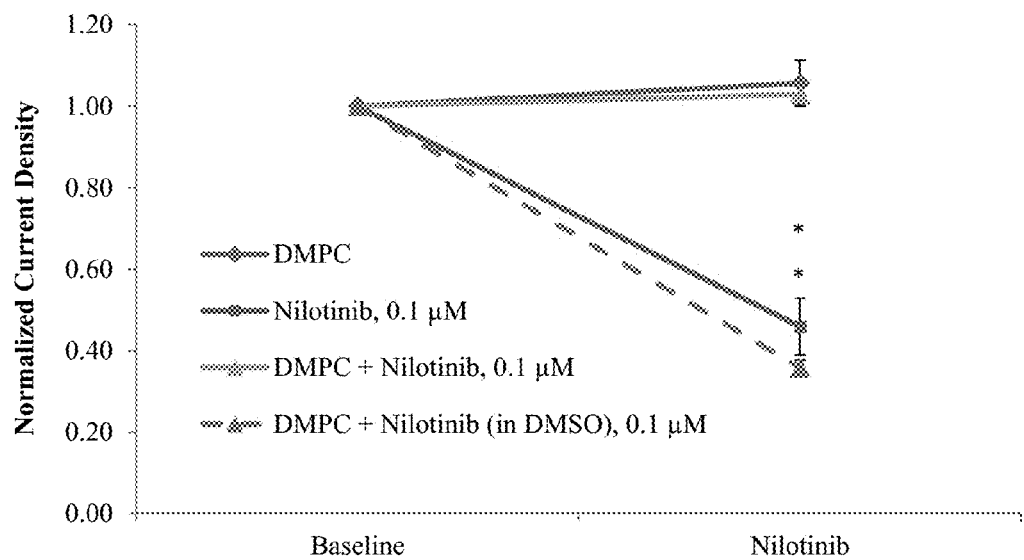
FIG. 6 is a graph that shows the effect of DMPC, DMPC+Nilotinib, DMPC+Nilotinib (in DMSO) and Nilotinib on hERG current density from transfected HEK 293 cells.

FIG. 6 is a graph that shows the effect of DMPC, DMPC+Nilotinib, DMPC+Nilotinib (in DMSO) and Nilotinib on hERG current density from transfected HEK 293 cells.

TABLE 7

Effect of DMPG, DMPG + Nilotinib, DMPG + Nilotinib (in DMSO) and Nilotinib on hERG current density from transfected HEK 293 cells.

| | Normalized Current Density | Corrected Normalized Current Density | SEM | p value | n = |
|---|---|---|---|---|---|
| Baseline | 1.000 | 1.000 | n/a | n/a | 3 |
| DMPG | 0.800 | 0.994 | 0.044 | 0.901 | 3 |
| Nilotinib, 0.1 μM | 0.308 | 0.459* | 0.070 | 0.016 | 3 |
| DMPG + Nilotinib, 0.1 μM | 0.743 | 0.936 | 0.067 | 0.437 | 3 |
| DMPG + Nilotinib (in DMSO), 0.1 μM | 0.630 | 0.823 | 0.290 | 0.651 | 2 |

Figure 7:
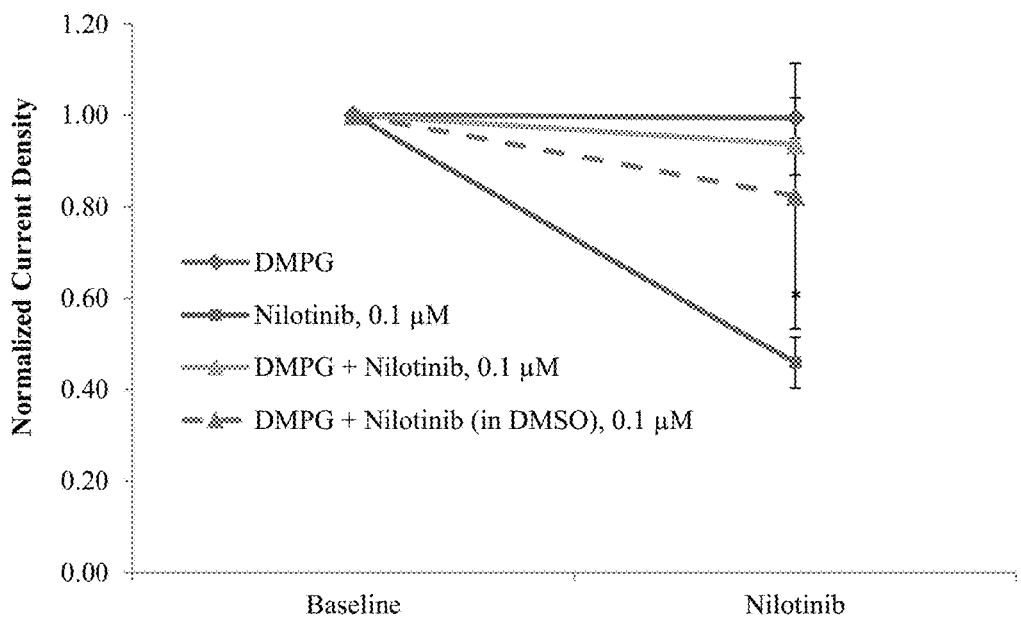
FIG. 7 is a graph that shows the effect of DMPG, DMPG+Nilotinib, DMPG+Nilotinib (in DMSO) and Nilotinib on hERG current density from transfected HEK 293 cells.

FIG. 7 is a graph that shows the effect of DMPG, DMPG+Nilotinib, DMPG+Nilotinib (in DMSO) and Nilotinib on hERG current density from transfected HEK 293 cells.

Oral formulation of a Liposome breakdown product mitigates intravenous Moxifloxacin induced QTc prolongation in vivo.

Structurally diverse anticancer drugs block the cardiac delayed rectifier K+ channel (IKr) encoded by the ether-a-go-go gene (hERG) resulting in acquired Long QT syndrome (LQTS). The probability of severe cardiac arrhythmia and sudden death is increased in patients medicated with LQTS-inducing anticancer drugs. This risk is a drug development hurdle and drugs have been withdrawn from the market or assigned black box warnings. During development of curcumin as an anticancer drug we confirmed it blocked the hERG channel in a concentration dependent manner with an $IC_{50}$ of 4.9 uM. This effect was abrogated by a solubilizing liposomal formulation consisting of 1,2-dimyristoyl-sn-glycero-3-phosphocholine (DMPC) and 1,2-dimyristoyl-sn-Glycero-3-[phosphoric-1-glycerol)]-sodium salt (DMPG). As shown hereinabove, this effect was seen with other LQTS-inducing drugs such as crizotinib, nilotinib and E4031 a methanesulfonamide anti-arrhythmic-inducing drug. Individual liposome components DMPC and DMPG and their breakdown products, given intravenously in rabbits and rats, abrogated the effects of nilotinib on the hERG channel in vitro. In the present study we tested the effects of an oral formulation of one of the breakdown products on the LQTS induced by moxifloxacin. Moxifloxacin is an antibiotic used to treat certain bacterial infections, including bronchitis, pneumonia, and sinus, skin, or stomach infections. Moxifloxacin is available as tablets and an intravenous injection Moxifloxacin intravenous injection and is for hospital use only.

Methods. The present inventors formulated the product in a complex mixture as an oral application in order to facilitate drug delivery in cancer patients being treated with oral LQTS inducing drugs. Preclinical evaluation of the oral application was done by instrumented Sprague Dawley male (250-300 g) rats. Cutaneous ECG leads were used to maximize T wave detection. The animals in groups of 3 rats were briefly anesthetized with a light dose of isoflurane, and a pre-treatment ECG was obtained to establish well-defined T waves, and to rule-out existing arrhythmic predispositions. Pre-treatment ECG profiles were normal.

A single dose of the oral complex in the ratio of 9:1 Moxifloxicin was vortexed continuously for 5 minutes to obtain an emulsion and immediately administered by gavage. Moxifloxacin, a broad spectrum antibiotic with documented LQTS activity, was formulated in DMSO and 2 hours afterwards infused intravenously (femoral canula) over 20 minutes at a starting dose of 2.8 mg/kg. ECGs were recorded from 5 minutes prior to and during the 20 minute infusion. Then the animals were dosed at 6.1 mg/kg over 20 minutes; then 20 mg/kg over 20 minutes. In a positive control group moxifloxacin was infused alone. In a second group of rats the complex was given orally 2 hours prior to the first dose of moxifloxacin. In a third group of rats the complex was given intravenously 5 minutes before each dose level of moxifloxicin.

Moxifloxacin, at 6.1 mg/kg and 20 mg/kg caused QTc prolongation of 30 and 48 ms respectively. The threshold for acceptability at the FDA is 30 ms, at which point a drug gets a black box QT prolongation label. 20 mg/kg of Moxifloxacin causes a life-threatening QT prolongation of 55 ms. Pre-treatment with the oral complex caused the QT prolongation to fall significantly to less than 11 ms for the 20 mg/kg moxifloxacin dose.

These findings further demonstrate that combining the oral complex with LQTS-inducing drugs may remove the clinical threat and the black box label of moxifloxicin and other LQTS prolonging drugs used in cancer patients.

Figure 8:
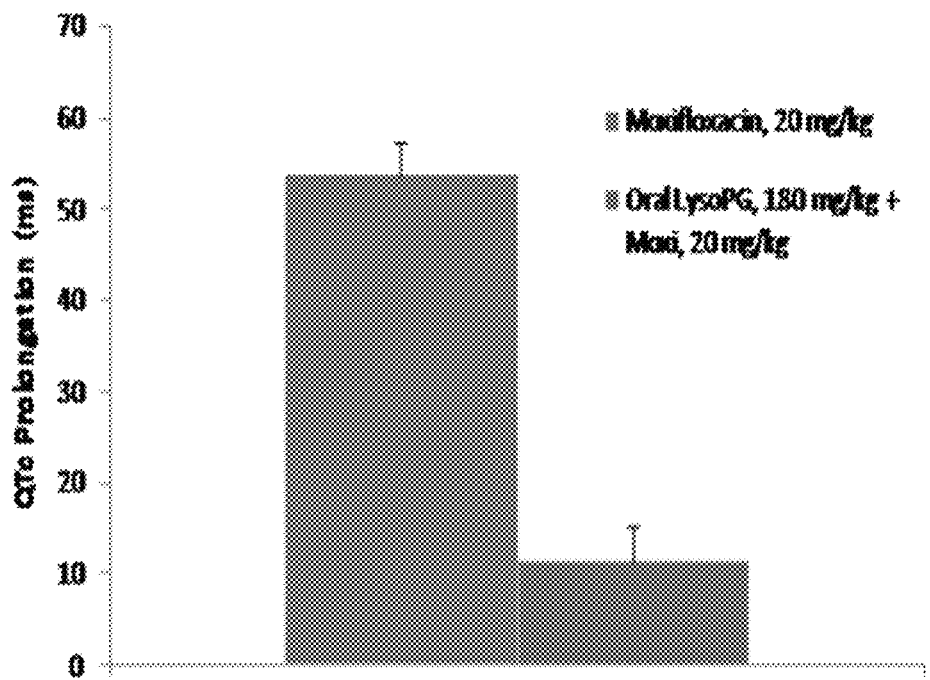
FIG. 8 is a graph that shows that the highest dose of Moxifloxacin (20 mg/kg) causes a life-threatening QT prolongation of 55 ms (the threshold for acceptability at the FDA is 30 ms, at which point a drug still gets a black QT label).

FIG. 8 is a graph that shows that at the highest dose of Moxifloxacin (20 mg/kg), which causes a life-threatening QT prolongation of 55 ms (the threshold for acceptability at the FDA is 30 ms, at which point a drug still gets a black QT label), the present invention eliminated the QTc prolongation.

Next, the inventors evaluated the protective effect of 10:0 Lyso PG, 12:0 Lyso PG, 14:0 Lyso PG, 16:0 Lyso PG, 18:0 Lyso PG and 14:0 EGPG against hERG inhibition by Nilotinib.

The purpose of this study is to evaluate in vitro the protective effect of 10:0 Lyso PG, 12:0 Lyso PG, 14:0 Lyso PG, 16:0 Lyso PG, 18:0 Lyso PG and 14:0 EGPG on the rapidly activating delayed-rectifier potassium selective current ($I_K$) generated under normoxic conditions in stably transfected Human Embryonic Kidney cells (HEK 293 cells).

Regulatory Compliance: This nonclinical laboratory study is designed as a screen and does not require QA involvement (non-GLP-compliant).

The test samples were as follows: 10:0 LysoPG+Nilotinib; 12:0 LysoPG+Nilotinib; 14:0 LysoPG+Nilotinib; 16:0 LysoPG+Nilotinib; 18:0 LysoPG+Nilotinib; 14:0 EGPG+Nilotinib.

The test samples were prepared as follows. The appropriate amount of Nilotinib powder was dissolved in an aqueous solution containing either 10:0 Lyso PG, 12:0 Lyso PG, 14:0 Lyso PG, 16:0 Lyso PG, 18:0 Lyso PG or 14:0 EGPG. The solution was vortexed for 10 minutes before being used in the patch-clamp assay.

All mixtures were a 9:1 ratio (lipid:nilotinib) on a molecular basis (mol:mol). Test System: hERG-expressing HEK 293 transfected cell line. Test performed: Whole-cell patch-clamp current acquisition and analysis. Temperature: 35±2° C. Original data acquisition design: Acquisition Rate(s): 1.0 kHz.

Patch-clamp current recording. Manual, whole-cell patch-clamp studies were conducted at physiological temperature on human embryonic kidney (HEK) cells, line 293 (HEK 293), stably transfected with the hERG gene (HEK-hERG). Isolated cells were plated into 2-mL experimental chambers, mounted on the platform of an inverted microscope. The cells were superfused with external solution (in mM: NaCl 140.0, KCl 5.0, $CaCl_2$ 1.8, $MgCl_2$ 1.0, HEPES 10.0, dextrose 10.0, pH 7.4±0.05). A 2-10 MΩ resistance pipette was filled with the pipette solution (in mM: KCl 140.0, $MgCl_2$ 1.0, Mg-ATP 4.0, EGTA 5.0, HEPES 10.0, sucrose 10.0, pH 7.4±0.05), and brought to contact the external membrane of a single cell.

Application of test samples: 5 minutes of exposure to each concentration in presence of closed circuit perfusion (2 mL/min). 5 minutes for washout periods in presence of a flow-through perfusion (2 mL/min) in addition to a closed circuit perfusion (2 mL/min). The positive control (Nilotinib, 1 µM) was added to naive cells obtained from the same cell line and same passage for a period of 5 minutes in presence of a closed circuit perfusion (2 mL/min). Cells were under continuous stimulation of the pulses protocol throughout the studies and cell currents were recorded after 5 minutes of exposure to each condition.

Design for acquisition when testing the compound or the vehicle/solvent equivalent: 1 recording made in baseline condition, 1 recording made in the presence of concentration 1.

Design for acquisition when testing the positive control: 1 recording made in baseline condition; 1 recording made in the presence of the positive control. n=number of responsive cells patched on which the whole protocol above could be applied.

Statistical analysis: Statistical comparisons were made using paired Student's t-tests, comparing each treatment period with its corresponding value at the baseline condition. The currents recorded after the exposure of each test sample were compared to the currents recorded in baseline conditions. Differences were considered significant when $p \leq 0.05$.

Exclusion criteria: (1) Timeframe of drug exposure not respected; (2) Instability of the seal; (3) No tail current generated by the patched cell; (4) No significant effect of the positive control; and/or (5) More than 10% variability in capacitance transient amplitude over the duration of the study.

Effect of the Test Samples on whole-cell IKr hERG currents. Whole-cell currents elicited during a voltage pulse were recorded in baseline conditions and following the application of the selected concentration of test sample. The cells were depolarized for one second from the holding potential (−80 mV) to a maximum value of +40 mV, starting at −40 mV and progressing in 10 mV increments. The membrane potential was then repolarized to −55 mV for one second, and finally returned to −80 mV.

Whole-cell tail current amplitude was measured at a holding potential of −55 mV, following activation of the current from −40 to +40 mV. Current amplitude was measured at the maximum (peak) of this tail current. Current density was obtained by dividing current amplitude by cell capacitance measured prior to capacitive transient minimization.

Current run-down and solvent effect correction. All data points presented in this example were corrected for solvent effect and time-dependent current run-down. Current run-down and solvent effects were measured simultaneously by applying the study design in test sample-free conditions over the same time frame as was done with the test sample. The loss in current amplitude measured during these so-called vehicle studies (representing both solvent effects and time-dependent run-down) was subtracted from the loss of amplitude measured in the presence of the test sample to isolate the effect of the test sample, apart from the effect of the solvent and the inevitable run-down in current amplitude over time.

TABLE 8

Effect of Nilotinib, 10:0 Lyso PG, 12:0 Lyso PG, 14:0 Lyso PG, 16:0 Lyso PG, 18:0 Lyso PG and 14:0 EGPG on hERG current density from transfected HEK 293 cells.

| | Normalized Current Density | Corrected Normalized Current Density | SEM | p value | n = |
|---|---|---|---|---|---|
| Baseline | 1.000 | 1.000 | n/a | n/a | 3 |
| Nilotinib (0.5 µg/mL) | 0.154 | 0.301* | 0.025 | 0.001 | 3 |
| 10:0 LysoPG (4.5 µg/mL) + Nilotinib (0.5 µg/mL) | 0.517 | 0.659* | 0.041 | 0.004 | 4 |
| 12:0 LysoPG (4.5 µg/mL) + Nilotinib (0.5 µg/mL) | 0.572 | 0.714* | 0.064 | 0.047 | 3 |
| 14:0 LysoPG (4.5 µg/mL) + Nilotinib (0.5 µg/mL) | 0.793 | 0.935 | 0.026 | 0.128 | 3 |
| 16:0 LysoPG (4.5 µg/mL) + Nilotinib (0.5 µg/mL) | 0.845 | 0.987 | 0.003 | 0.066 | 3 |
| 18:0 LysoPG (4.5 µg/mL) + Nilotinib (0.5 µg/mL) | 0.347 | 0.488* | 0.064 | 0.015 | 3 |
| 14:0 EGPG (4.5 µg/mL) + Nilotinib (0.5 µg/mL) | 0.675 | 0.817 | 0.044 | 0.054 | 3 |

Figure 9:
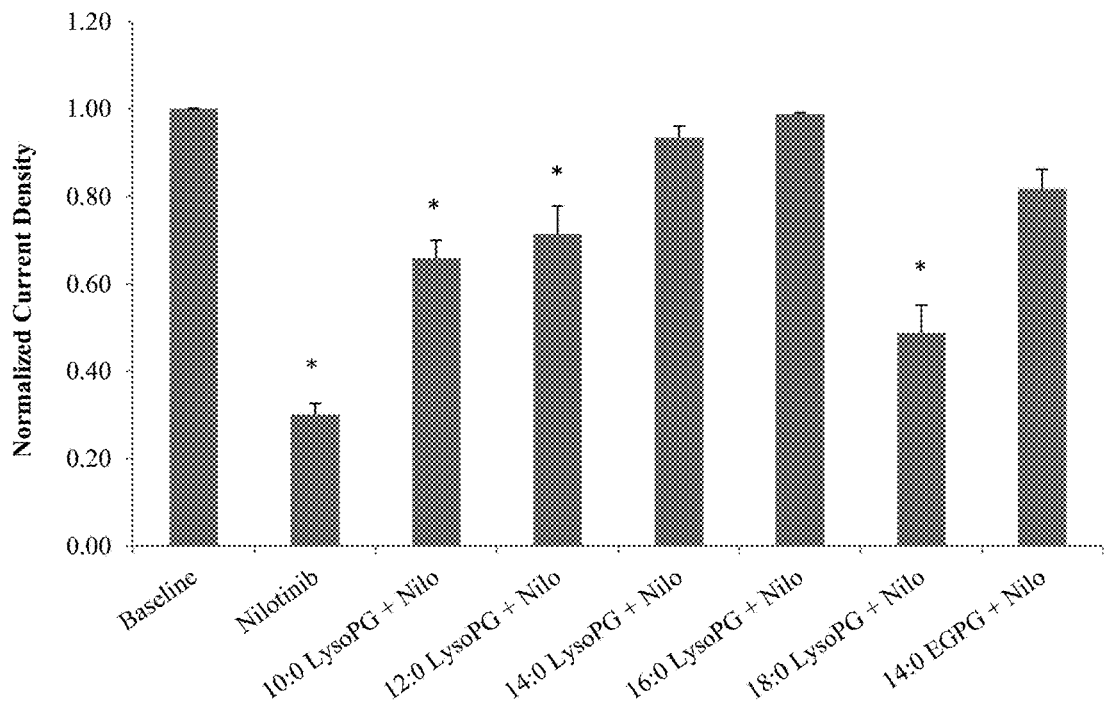
FIG. 9 is a graph that shows the effect of Nilotinib, 10:0 Lyso PG, 12:0 Lyso PG, 14:0 Lyso PG, 16:0 Lyso PG, 18:0 Lyso PG, and 14:0 EGPG, on hERG current density from transfected HEK 293 cells.

FIG. 9 is a graph that shows the effect of Nilotinib, 10:0 Lyso PG, 12:0 Lyso PG, 14:0 Lyso PG, 16:0 Lyso PG, 18:0 Lyso PG and 14:0 EGPG on hERG current density from transfected HEK 293 cells, and summarizes the data in Table 8.

The protective effect of 10:0 Lyso PG, 12:0 Lyso PG, 14:0 Lyso PG, 16:0 Lyso PG, 18:0 Lyso PG and 14:0 EGPG was determined against the inhibition of the rapidly activating delayed-rectifier potassium selective current ($I_{Kr}$) generated under normoxic conditions in stably transfected Human Embryonic Kidney (HEK) 293 cells caused by the Nilotinib. It was found that LysoPG of different carbon chain lengths (10:0, 12:0, 14:0, 16:0 and 18:0) and 14:0 EGPG alone did not cause any inhibition of the hERG tail current density. It was found that 1 µM Nilotinib caused 70% of inhibition of the hERG current. Nilotinib (Nilo) when formulated with 10:0, 12:0, 14:0, 16:0 and 18:0 LysoPG and 14:0 EGPG (phospholipids (PLs):Nilotinib (Nilo) or PLs/Nilo ratio: 9:1) prevented the inhibition of the hERG current. 14:0 and 16:0 LysoPG were the most potent PLs against the inhibition of hERG currents by Nilotinib.

All data points were corrected for solvent effects and time-dependent current run-down. These two parameters were evaluated by applying exactly the same design to the vehicle as with the control samples. The currents were measured over the same time course as was done in the presence of the test sample. The values obtained, representing both solvent effects and time-dependent run-down, were used to correct the effect of the test samples, if any. This ensures that changes attributable to time or the solvent are not mistakenly attributed to the test samples.

Nilotinib when formulated in an aqueous solution containing 10:0 Lyso PG, 12:0 Lyso PG, and 18:0 Lyso PG (ratio 9:1) (4.5 µg/mL lipid: 0.5 µg/mL nilotinib) cause 34.1, 28.6 and 51.2% of inhibition of the hERG tail current respectively.

Nilotinib when formulated in an aqueous solution containing 14:0 Lyso PG, 16:0 Lyso PG, and 14:0 EGPG (ratio 9:1) (4.5 µg/mL lipid: 0.5 µg/mL nilotinib) did not cause any inhibition of the hERG tail current.

Nilotinib alone, formulated in DMSO at 1 µM (or 0.5 µg/mL), caused 70% of inhibition of the hERG tail current (n=3). The inhibition observed is in line with previous data generated in identical conditions, and agrees with reported inhibition values for this compound.

These data show that, surprisingly, co-formulating Nilotinib with 14:0 Lyso PG, 16:0 Lyso PG, and 14:0 EGPG have a higher protective against hERG inhibition caused by Nilotinib, with a lesser effect shown for the other combinations. The skilled artisan will recognize that varying the ratios of the agent that causes a channelopathy and the Lyso forms of the various lipids can be optimized following the teachings hereinabove.

Figure 10:
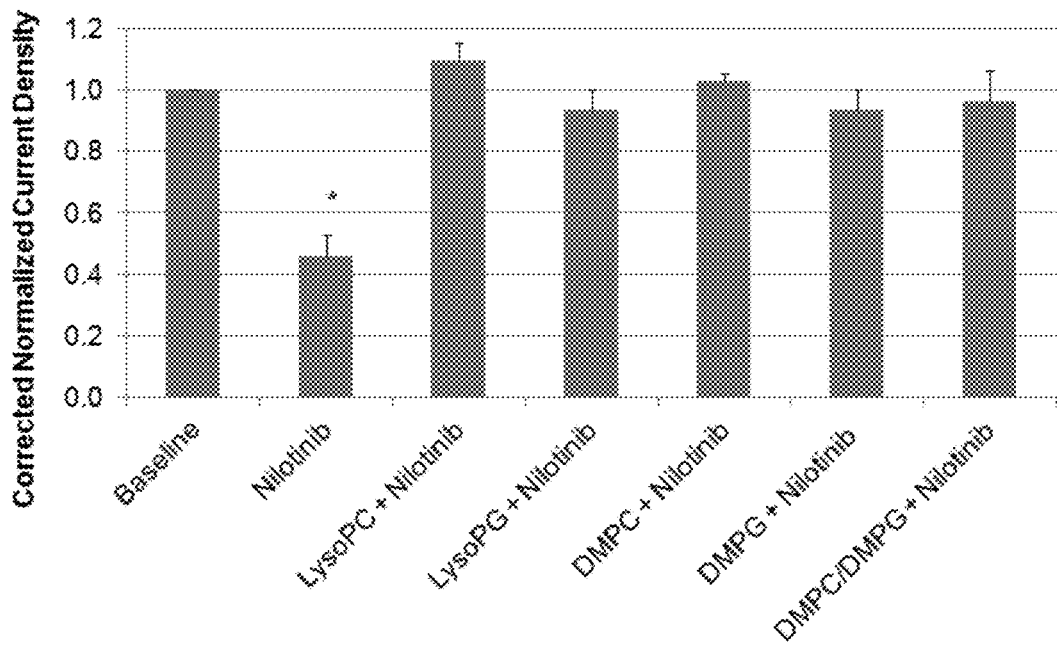
FIG. 10 shows the removal of IKr inhibition by various phospholipids (PLs).

FIG. 10 shows the removal of IKr inhibition by various phospholipids (PLs). Liposomes made with DMPC, DMPG, DMPC/DMPG, LysoPC and LysoPG did not cause any inhibition of the hERG tail current density. Nilotinib alone at 0.1 µM caused 54% of inhibition of the hERG current. Nilotinib co-formulated with DMPC, DMPG, DMPC/DMPC, LysoPC or LysoPG (Nilo/PLs ratio: 9:1) no longer inhibited the hERG tail current. DMPC: 1,2-dimyristoyl-sn-glycero-3-phosphocholine; DMPG: 1,2-dimyristoyl-sn-glycero-3-[phosphoric-(1-glycerol)].

In Vivo Examples.

Male Hartley guinea pigs (350-400; Charles River) were used in these studies. The animals were anaesthetized with a mixture of 1.0 to 1.5% isoflurane USP in 95% $O_2$ and 5% $CO_2$. The jugular vein was cannulated for intravenous (i.v) infusion of 20 mg/kg moxifloxacin (MF). ECG leads were placed on the animals in a 3-lead configuration.

The blended eutectic EU8120, 14:0 LysoPG, 16:0 LysoPG, 14:0 EGPG; and DMPG (Avanti Polar Lipids, Inc.) were administrated as an oral gavage 2 hours prior to the infusion of MF. Three animals were exposed to each PL+MF combination at PLs/MF ratios of 3:1, 1:1 or 0.3:1 (n=3).

Figure 11A:
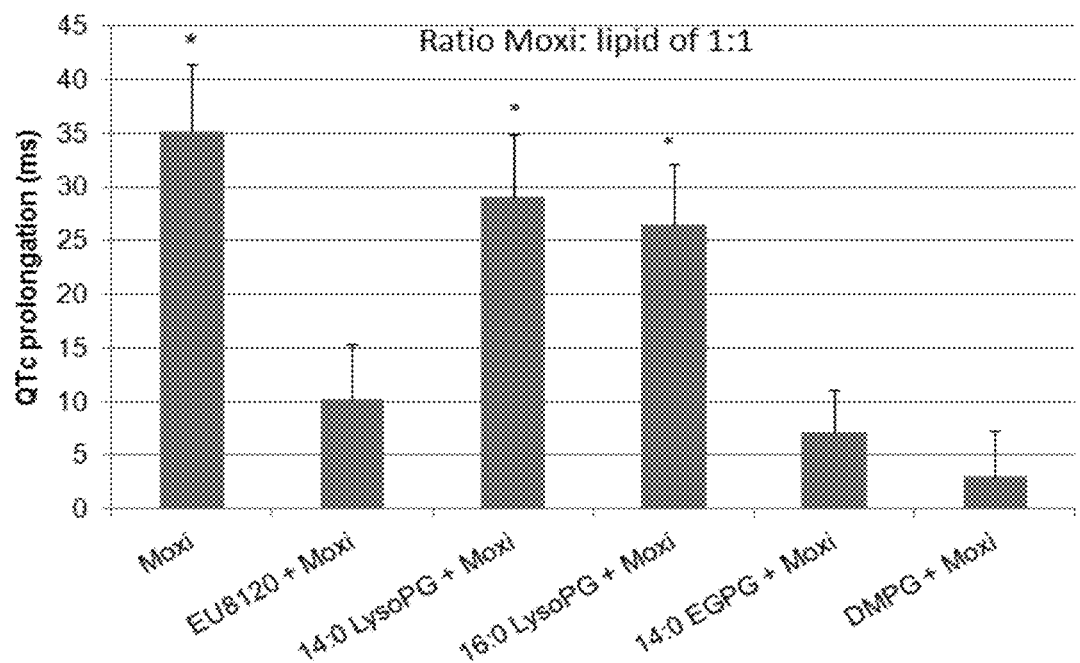
FIG. 11A is a graph that shows the mitigation of QT prolongation by various PLs liposomes at a PL to drug ratio of 1:1.

FIG. 11A is a graph that shows the mitigation of QT prolongation by various PLs liposomes. Briefly, 20 mg/kg i.v. MF caused a 35-ms QTc prolongation in guinea pigs. EU8120, 14:0 EGPG, and DMPG prevented the MF-induced QTs prolongation.

Figure 11B:
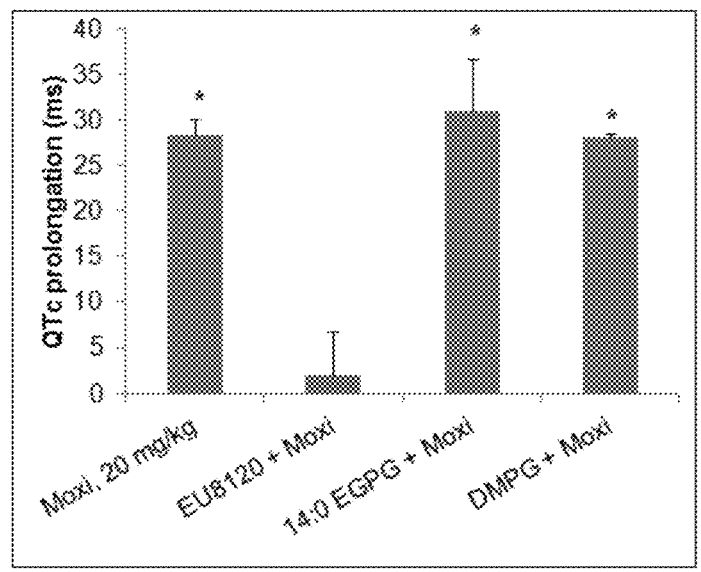
FIG. 11B is a graph that shows that dropping the phospholipids (PLs):moxifloxacin (MF) ratio (PLs:MF ratio) to 0.3:1 revealed the efect of a blended eutectic.

FIG. 11B is a graph that shows that dropping the PLs:MF ratio to 0.3:1 revealed the greater potency of EU8120. EU8120 maintains its efficacy down to a ratio of 0.3:1.

Figure 12:
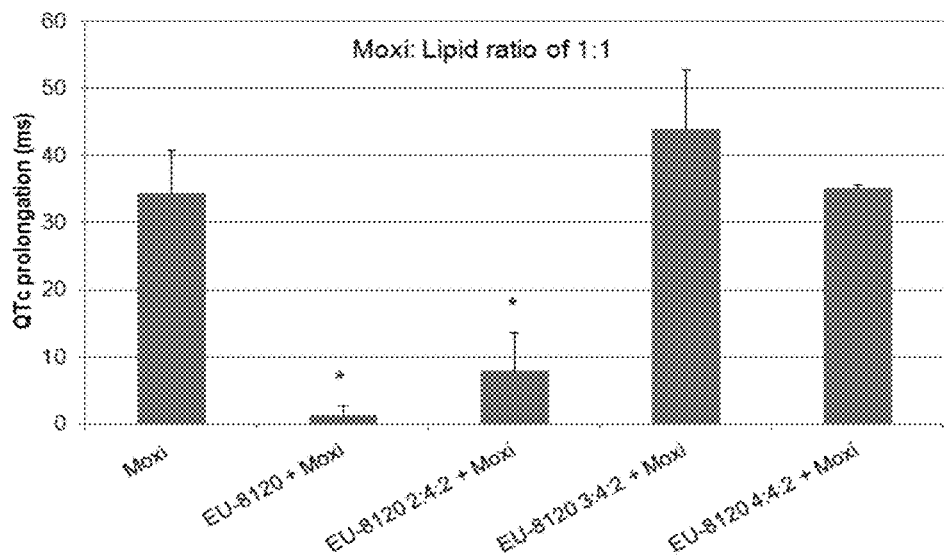
FIG. 12 shows the QTc-based optimization of a blended eutectic.

FIG. 12 shows the QTc-based optimization of EU8120. In one non-limiting example, EU8120 was constituted of a 1:4:2 ratio of 14:0 LysoPG/myristoyl monoglyceride/myristic fatty acid chain. Changing the constituent ratio to 2:4:2, 3:4:2, 4:4:2 (i.e., increasing the LysoPG content of EU8120) resulted in a loss of QTc mitigation potency. It may be, but is not a limitation of the present invention, that myristoyl monoglyceride and myristic acid are necessary for oral bioavailability. These same methodology taught herein can be used to determine the effect of substituting the monoglyceride and fatty acid constituents on QTc mitigation potency.

Figure 13:
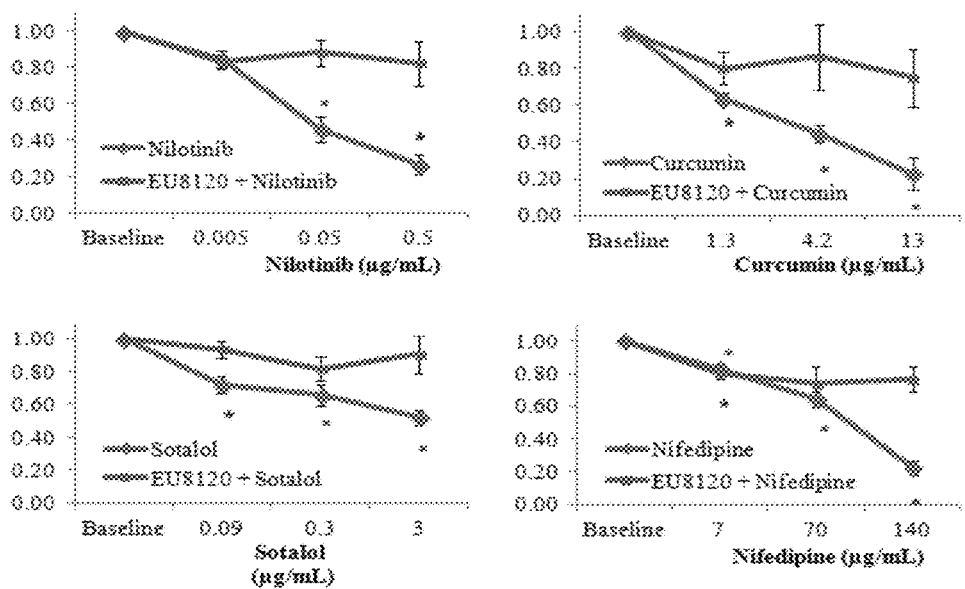
FIG. 13 shows four graphs that show the effect of a blended eutectic prevents IKr inhibition via lipid-receptor interactions with Nitolinib, Curcum, Sotabol and Nifedipine.

FIG. 13 is a graph that shows that EU8120 prevents IKr inhibition via lipid-receptor interactions. The compositions of the present invention were combined with nilotinib (anticancer), curcumin (broad spectrum active agent), sotalol (anti-arrythmic) and nifedipine (calcium channel blocker) and each shows a dose dependent response. Flat concentration-response curves for some drugs suggest receptor-lipid interactions. By way of explanation, and in no way a limitation of the present invention, the receptor is likely the hERG channel, with EU8120 binding a site within the pore of the channel, or a site within the cytoplasmic membrane.

Figure 14:
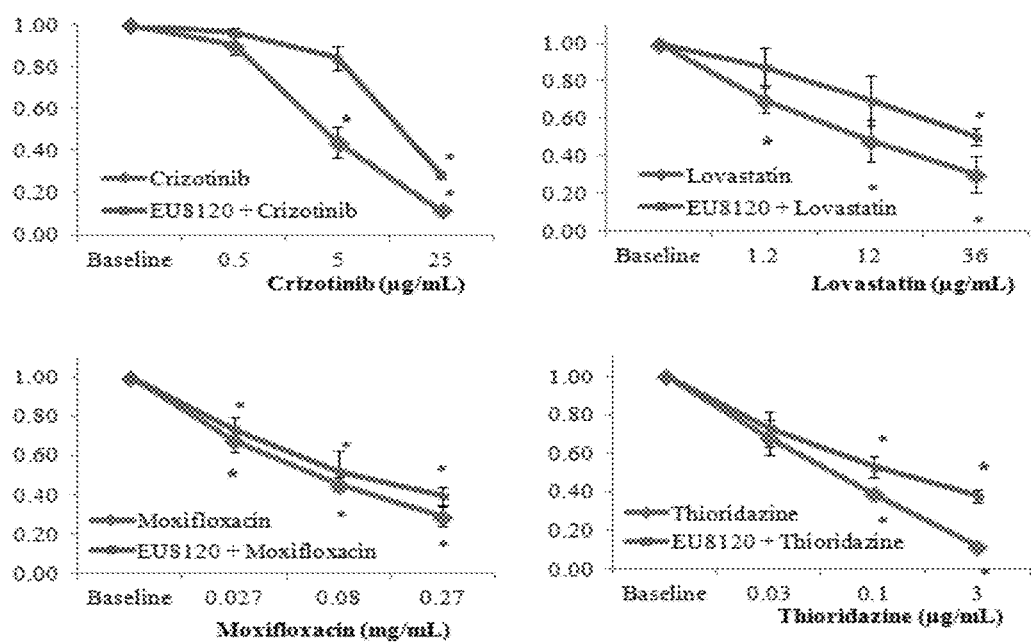
FIG. 14 shows four graphs that show a blended eutectic prevents IKr inhibition via PL-drug interactions with Crizotinib, Lovastatin, Moxifloxacin and Thioridazine.

FIG. 14 is a graph that shows that EU8120 prevents IKr inhibition via PL-drug interactions. The compositions of the present invention were combined with crizotinib (anticancer), lovastatin (statin, cholesterol reduction), moxifloxacin (antibacterial agent), and thioridazine (antipsychotic drug) and shows that inhibition was proportional to the amount of the eutectic mixture EU8120. By way of explanation, and in no way a limitation of the present invention, the concentration-response curves suggest a PL-drug interaction for some drugs. Inhibition was found to be proportional to the amount of EU8120 and appears independent of a membrane-based receptor.

A formulation of 14:0 LPG in a eutectic mixture with a myristoyl monoglyceride and myristic acid (EU8120) given orally to guinea pigs prior to intravenous (i.v.) infusion of anticancer agents (nilotinib and crizotinib) and an antibacterial agent (moxifloxacin) resulted in significantly reduced QTc prolongation. Four ratios of PLs/MF were tested for mitigation of conduction delays: 3:1, 1:1, 0.3:1, and 0.1:1.

Figure 15:
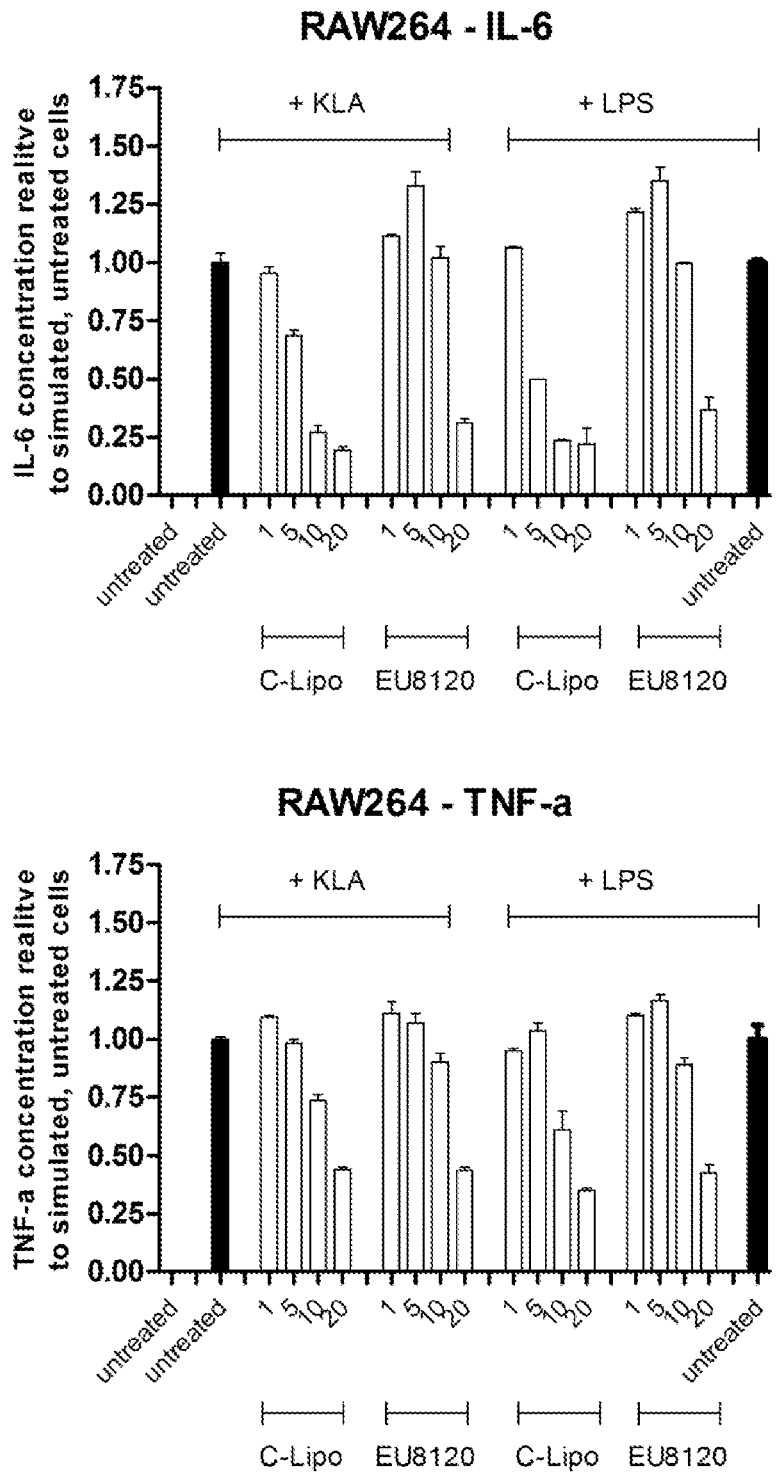
FIG. 15 shows the cytokine release data (IL-6 and TNF-α) comparing the effect of empty liposomes (C-Lipo) with the Eutectic EU8120.

EU8120 has further uses. FIG. 15 shows the cytokine release data (IL-6 and TNF-α) comparing the effect of empty liposomes (C-Lipo) with the eutectic EU8120. The EU8120 used was constituted of a 1:4:2 ratio of 14:0 LysoPG/myristoyl monoglyceride/myristic chain. EU8120 was dissolved in water (stock 4 mM) and extensively vortexed before being added to the cells. RAW264 macrophages were pre-incubated for 24 h with empty liposomes or EU8120 before being stimulated for 24 h with KDO2 (10 ng/ml) or LPS (100 ng/ml). These data show that EU8120 like empty liposomes inhibited IL-6 and TNF-α production in KDO2 and LPS-stimulated macrophage, however, EU8120 has the advantage that it can be provided orally. Empty liposomes and EU8120 were used at concentrations from 1-20 microM.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

U.S. Patent Publication No. 2010/0004549: System and Method of Serial Comparison for Detection of Long QT Syndrome (LQTS).

U.S. Patent Publication No. 2008/0255464: System and Method for Diagnosing and Treating Long QT Syndrome.

U.S. Patent Publication No. 2007/0048284: Cardiac Arrhythmia Treatment Methods.

U.S. Patent Publication No. 2001/00120890: Ion Channel Modulating Activity I.

What is claimed is:

1. A method for preventing or treating at least one of IKr channel inhibition or QT prolongation arising from administration of one or more active agents that causes an active agent-induced channelopathy in a human or animal subject comprising the steps of:
identifying the human or animal subject in need of prevention or treatment of a disease treatable with an active agent that causes a drug-induced channelopathy;
providing an amount of a lysophosphatidyl compound adapted for oral administration effective to reduce or prevent one or more cardiac channelopathies or conditions resulting from irregularities or alterations in cardiac patterns caused by one or more active agents, wherein the lysophosphatidyl compound is selected from at least one of 10:0 LysoPG, 12:0 LysoPG, 14:0 LysoPG, 14:0 EGPG, 16:0 LysoPG, or 18:0 LysoPG, wherein the lysophosphatidyl compound enhances the activity of the active agent; and
administering to the human or animal subject a therapeutically effective amount of an active agent that causes an active agent-induced channelopathy, wherein the oral lysophosphatidyl compound reduces or eliminates the channelopathy induced by the therapeutically active agent.

2. The method of claim 1, wherein the active agent has previously failed a clinical trial due to drug-induced IKr channel inhibition or QT prolongation.

3. The method of claim 1, further comprising the step of identifying a drug in a clinical trial that failed or has limited clinical use due to drug-induced IKr channel inhibition or QT prolongation side-effects.

4. The method of claim 1, wherein the one or more active agents are selected from Albuterol (salbutamol), Alfuzosin, Amantadine, Amiodarone, Amisulpride, Amitriptyline, Amoxapine, Amphetamine, Anagrelide, Apomorphine, Arformoterol, Aripiprazole, Arsenic trioxide, Astemizole, Atazanavir, Atomoxetine, Azithromycin, Bedaquiline, Bepridil, Bortezomib, Bosutinib, Chloral hydrate, Chloroquine, Chlorpromazine, Ciprofloxacin, Cisapride, Citalopram, Clarithromycin, Clomipramine, Clozapine, Cocaine, Crizotinib, Dabrafenib, Dasatinib, Desipramine, Dexmedetomidine, Dexmethylphenidate, Dextroamphetamine (d-Amphetamine), Dihydroartemisinin and piperaquine, Diphenhydramine, Disopyramide, Dobutamine, Dofetilide, Dolasetron, Domperidone, Dopamine, Doxepin, Dronedarone, Droperidol, Ephedrine, Epinephrine (Adrenaline), Eribulin, Erythromycin, Escitalopram, Famotidine, Felbamate, Fenfluramine, Fingolimod, Flecainide, Fluconazole, Fluoxetine, Formoterol, Foscarnet, Fosphenytoin, Furosemide (Frusemide), Galantamine, Gatifloxacin, Gemifloxacin, Granisetron, Gripafloxacin, Halofantrine, Haloperidol, Hydrochlorothiazide, Ibutilide, Iloperidone, Imipramine (melipramine), Indapamide, Isoproterenol, Isradipine, Itraconazole, Ivabradine, Ketoconazole, Lapatinib, Levalbuterol (levsalbutamol), Levofloxacin, Levomethadyl, Lidoflazine, Lisdexamfetamine, Lithium, Mesoridazine, Metaproterenol, Methadone, Methamphetamine (methamfetamine), Methylphenidate, Midodrine, Mifepristone, Mirabegron, Mirtazapine, Moexipril/HCTZ, Moxifloxacin, Nelfinavir, Nicardipine, Nilotinib, Norepinephrine (noradrenaline), Norfloxacin, Nortriptyline, Ofloxacin, Olanzapine, Ondansetron, Oxytocin, Paliperidone, Paroxetine, Pasireotide, Pazopanib, Pentamidine, Perflutren lipid microspheres, Phentermine, Phenylephrine, Phenylpropanolamine, Pimozide, Posaconazole, Probucol, Procainamide, Promethazine, Protriptyline, Pseudoephedrine, Quetiapine, Quinidine, Quinine sulfate, Ranolazine, Rilpivirine, Risperidone, Ritodrine, Ritonavir, Roxithromycin, Salmeterol, Saquinavir, Sertindole, Sertraline, Sevoflurane, Sibutramine, Solifenacin, Sorafenib, Sotalol, Sparfloxacin, Sulpiride, Sunitinib, Tacrolimus, Tamoxifen, Telaprevir, Telavancin, Telithromycin, Terbutaline, Terfenadine, Terodilene, Tetrabenazine, Thioridazine, Tizanidine, Tolterodine, Toremifene, Trazodone, Trimethoprim-Sulfa, Trimipramine, Vandetanib, Vardenafil, Vemurafenib, Venlafaxine, Voriconazole, Vorinostat, or Ziprasidone.

5. The method of claim 1, further comprising the step of forming a eutectic mixture with the lysophosphatidyl compound.

6. The method of claim 5, wherein the eutectic mixture comprises a free fatty acid and monoglyceride that comprise from about 70 mole to 99 mole percent of the eutectic mixture, with the lysophosphatidyl compound comprising from about 30 mole percent to 1 mole percent of the eutectic mixture.

7. The method of claim 6, wherein the ratios of the components of the eutectic mixture are 1:4:2, a 1:3:3, a 2:4:2, or a 1:2:4 mole percent lysophosphatidyl compound:monoglyceride:free fatty acid.

8. The method of claim 1, further comprising the step of forming a eutectic mixture with the lysophosphatidyl compound, wherein the eutectic mixture comprises LysoPG:myristoyl monoglyceride:myristic fatty.

9. The method of claim 1, wherein a ratio of the lysophosphatidyl compound to active agent is 3:1, 1:1, 0.3:1, and 0.1:1.

10. A method for preventing or treating at least one of IKr channel inhibition or QT prolongation arising from administration of one or more active agents that causes an active agent-induced channelopathy in a human or animal subject comprising the steps of:
- identifying the human or animal subject in need of prevention or treatment of a disease treatable with the one or more active agent that causes a drug-induced channelopathy;
- providing an amount of a lysophosphatidyl compound adapted for oral administration effective to reduce or prevent one or more cardiac channelopathies or conditions resulting from irregularities or alterations in cardiac patterns caused by one or more active agents, wherein the lysophosphatidyl compound is selected from at least one of 10:0 LysoPG, 12:0 LysoPG, 14:0 LysoPG, 14:0 EGPG, 16:0 LysoPG, 18:0 LysoPG, or a eutectic thereof, wherein the lysophosphatidyl compound enhances the activity of the active agent; and
- administering to the human or animal subject a therapeutically effective amount of an active agent that causes an active agent-induced channelopathy, wherein the oral lysophosphatidyl compound reduces or eliminates the channelopathy induced by the therapeutically active agent.

\* \* \* \* \*